US008802442B2

(12) United States Patent
Wheeldon et al.

(10) Patent No.: US 8,802,442 B2
(45) Date of Patent: Aug. 12, 2014

(54) APPARATUS AND METHOD FOR THE REMOTE SENSING OF BLOOD IN HUMAN FECES AND URINE

(71) Applicants: Eric B. Wheeldon, Swarthmore, PA (US); Robert J. Barsotti, Philadelphia, PA (US)

(72) Inventors: Eric B. Wheeldon, Swarthmore, PA (US); Robert J. Barsotti, Philadelphia, PA (US)

( * ) Notice: Subject to any disclaimer, the term of this patent is extended or adjusted under 35 U.S.C. 154(b) by 0 days.

(21) Appl. No.: 13/688,803

(22) Filed: Nov. 29, 2012

(65) Prior Publication Data

US 2014/0147924 A1    May 29, 2014

Related U.S. Application Data

(60) Provisional application No. 61/565,085, filed on Nov. 30, 2011.

(51) Int. Cl.
| | |
|---|---|
| *G01N 21/75* | (2006.01) |
| *G01N 21/76* | (2006.01) |
| *G01N 33/72* | (2006.01) |
| *G01N 33/48* | (2006.01) |

(52) U.S. Cl.
CPC ..................................... *G01N 21/75* (2013.01)
USPC ............... 436/66; 436/63; 436/164; 436/172; 422/52; 422/82.05; 422/82.08; 250/459.1

(58) Field of Classification Search
CPC .............. C12Q 1/00; C12Q 1/02; C12Q 3/00; C12Q 2304/00; G01N 21/75; G01N 21/76; G01N 33/48; G01N 33/49; G01N 33/72; G01N 33/721; G01N 33/725; G01N 33/726; G01N 2333/805
USPC ........ 436/63, 66, 164, 165, 166, 172; 422/52, 422/68.1, 82.05, 82.08; 435/29, 287.1, 435/288.7; 702/22, 27, 28, 31; 250/458.1, 250/459.1

See application file for complete search history.

(56) References Cited

U.S. PATENT DOCUMENTS 4,860,767 A    8/1989    Maekawa
(Continued)

FOREIGN PATENT DOCUMENTS

| | | |
|---|---|---|
| DE | 3044878 | 7/1982 |
| JP | 62-177450 | 8/1987 |

(Continued)

*Primary Examiner* — Maureen Wallenhorst
(74) *Attorney, Agent, or Firm* — Lipton, Weinberger & Husick; Robert J. Yarbrough

(57) ABSTRACT

The apparatus and method for detecting blood in urine or feces includes a photodetector configured to detect a transient light emitted in a toilet bowl by luminol and an oxidizer catalyzed by iron in the blood. The apparatus may include dispensers for the luminol, the oxidizer and a base. The apparatus may include a microprocessor and a network connection and may perform statistical analyzes, store data and alert the patient or a healthcare provider if blood is detected. The photodetector may be configured to detect light emitted in the toilet bowl by a fluorophore present in the water and excited by the transient light from the luminol and oxidizer.

47 Claims, 20 Drawing Sheets

(56) References Cited

U.S. PATENT DOCUMENTS

Figure 1:
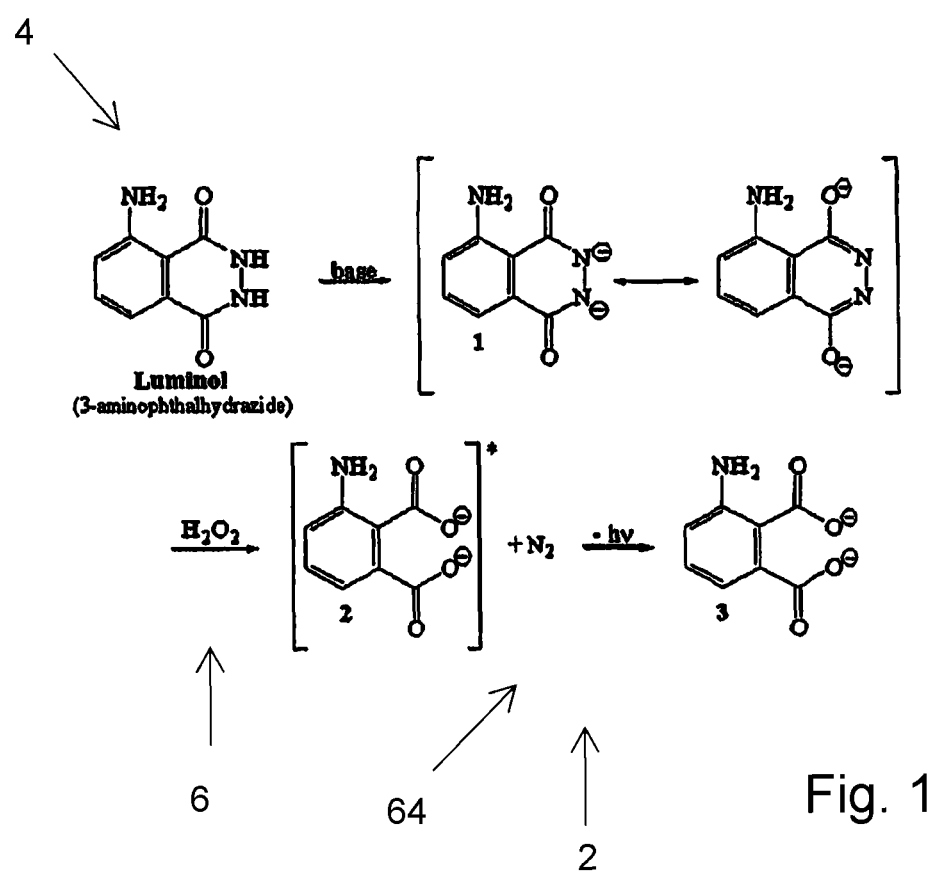

| | | |
|---|---|---|
| 5,073,500 A | 12/1991 | Saito |
| 5,081,040 A | 1/1992 | Patel |
| 5,196,167 A | 3/1993 | Guadagno |
| 5,198,192 A | 3/1993 | Saito |
| 5,455,971 A | 10/1995 | Sakakibara |
| 5,772,606 A | 6/1998 | Ashibe |
| 7,241,578 B2 | 7/2007 | Yugawa |
| 2001/0032098 A1* | 10/2001 | Kulkarni .......................... 705/2 |
| 2004/0194206 A1 | 10/2004 | Kieturakis |

FOREIGN PATENT DOCUMENTS

| | | | |
|---|---|---|---|
| JP | 63-247659 | | 10/1987 |
| JP | 5-2017 | * | 1/1993 |
| JP | 5-273206 | * | 10/1993 |
| JP | 09302749 | | 11/1997 |
| WO | 2011/123776 | * | 10/2011 |

* cited by examiner

| Item | Description | Qty |
|---|---|---|
| 1 | Ceramic Substrate | 1 |
| 2 | Op AMP - Analog Devices, OP-549LH. 8 Lead | 1 |
| 3 | Resistor, Radial-Leaded, 10G - Variable, +/-2% | 1 |
| 4 | Capacitor, SMD 1812, 100pF, 500V | 1 |
| 5 | Resistor, SMD, 1206, 100K +/-5% | 1 |
| 6 | Resistor, SMD, 1206, resistance dependent on OPAMP, +/- 5% | 1 |
| 7 | Potentiometer, 10K, single turn | 1 |
| 8 | Capacitor, SMD 1206, 0.1µF, +/- 10% | 2 |
| 9 | Teflon Wire, Multi Strand, 22 AWG | 4 |
| 10 | Silicon Photodiode, AXUV-100, IRD Torrance Ca | 1 |
| 11 | Receptacle Pin | 2 |
| 12 | Band Pass Filter - 450nm +/- 40nm | 1 |

Fig. 6

APPARATUS AND METHOD FOR THE REMOTE SENSING OF BLOOD IN HUMAN FECES AND URINE

I. RELATED APPLICATIONS

This application claims priority from U.S. Provisional Patent Application 61/565,085 by the inventors herein filed Nov. 30, 2011.

II. BACKGROUND OF THE INVENTION

A. Field of the Invention

The Invention is an apparatus and method for detecting blood in feces or urine in water in a toilet bowl for the purpose of non-invasive medical monitoring or screening. The blood may be occult or non-occult.

B. Description of the Related Art

According to the National Cancer Institute, colorectal cancer (CRC) is the second leading cause of cancer related mortality in the United States, with around 148,500 new cases per year and about 56,000 deaths, accounting for 10% of all cancer-related deaths in the US. It is believed that more than 50% of these deaths may have been prevented through the use of better and earlier screening tests. However, compliance with current screening recommendations and procedures is poor. For example in 2002 only 40% of adults aged 50 years and older had either a sigmoidoscopy or colonoscopy in the last 5 years and only 22% had received a fecal occult blood test in the past 12 months. The low rate of participation in CRC screening especially in comparison to breast and cervical cancer screening is due to a number of factors, including patient discomfort, cost, lack of awareness, and poor acceptability of current screening methods.

Colorectal cancer prognosis worsens significantly with advanced disease. Patients with metastases (stage IV) have only a 5% five-year survival rate. Patients with early disease (stage I) have over a 90% five-year survival rate. With the prognosis for advanced disease so poor and survival for early disease so favorable, early detection remains the primary option for CRC control and a simple, noninvasive reliable screening method for early detection of colorectal cancer has been a long-standing goal.

Detection of blood in fecal material can serve as a screening tool for CRC since these tumors bleed readily and so can be discovered at an early stage. The presence of blood alerts the patient to visit a doctor to evaluate the source of the blood.

Prior art screening tests for fecal blood include the stool guaiac test, fecal immunochemical testing (FIT), immunochemical fecal occult blood test (iFOBT), fecal porphyrin quantification, and fecal DNA testing. However, all require the handling of fecal material. For example, in the stool guaiac test, fecal material from a digital rectal examination or from soiled toilet tissue is smeared on a paper that is attached to a film coated with guaiac. Hydrogen peroxide is applied to the opposite side of the film. The hydrogen peroxide and the guaiac react. The reaction is catalyzed by heme, a component of hemoglobin in blood. The reaction causes a rapid color change if blood is present.

Detection of blood in urine can also be useful in screening for bladder cancer. Bladder cancer is the fourth most commonly diagnosed cancer in men and the ninth most commonly diagnosed cancer in women in the United States. An estimated 70,980 new cases of bladder cancer were diagnosed in the United States during 2009, and approximately 14,330 people died of the disease. Bladder tumors classically produce painless hematuria as their dominant and sometimes only clinical manifestation. Consequently, an estimated one fourth of all cases of bladder cancer have already metastasized at the time of diagnosis. Again, a simple non-invasive and reliable method of screening could identify bladder cancer at earlier stages, when it may be more easily and effectively treated.

Current techniques for detecting blood in urine include 'dipstick' tests in which a test strip is wetted with a urine sample and the color change of the test strip noted. The dipstick test requires that a technician physically handle the dipstick and place the dipstick in direct contact with the urine.

The prior art does not teach the screening apparatus or method of the invention.

III. SUMMARY OF THE INVENTION

The invention is an apparatus and method for the remote detecting blood in fecal material or urine in water in a toilet bowl. The apparatus and method comprise a screening test that can be utilized by a patient in the patient's home or in any other location. The patient is not required to physically touch the fecal material or urine. In some embodiments, the patient is not required to even see the fecal material or urine.

The apparatus and method of the Invention utilizes the light-producing reaction between luminol ($C_8H_3N_3O_2$), which is chemiluminescent, and an oxidizer in a toilet bowl. To conduct the test of the invention, the patient prepares the water of the toilet bowl by adding three materials to the water prior to defecating or urinating (or both). In some embodiments, the three materials may be added to the water after the patient urinates or defecates.

The first material added is a sufficient amount of luminol to achieve an effective molar concentration of luminol in the toilet bowl water. A luminol concentration of 50 millimoles per liter (mM) is known to be effective and a luminol concentration of between 1 and 200 mM is believed to be effective. The first material also may include one or more fluorophores, which are fluorescent materials as is known in the art. As used in this document and in the claims, a fluorophore is a material that when present in water and bombarded by photons emitted by the luminol-oxidizer reaction or by another fluorophore fluoresces and emits light. As used in this document and in the claims, the term 'luminol' includes luminol and also includes a combination of luminol one or more fluorophores. Examples of fluorophores include fluorescein, Bodipy, Cy 3 and Cy5.

The second material is a base, which may be combined with the luminol. The amount of base introduced into the toilet bowl is enough to achieve an adequately basic pH in the toilet bowl water to allow the reaction to proceed. A basic pH of between 10 and 11 is believed to be optimal. A molar concentration of between 50 and 3000 mM of sodium borate is believed to be suitable to achieve the desired basic pH. Other acceptable bases include sodium hydroxide, potassium hydroxide, potassium carbonate and sodium carbonate.

The second material may be an alkaline buffer, as is known in the art, preferably an alkaline buffer having a pH range of between 9 and 12. Any other alkaline buffer having a pH range that is effective to allow the luminol-oxidizer reaction to proceed may be selected. Alkaline buffers that are believed to be suitable include those known by the acronyms 'trizma,' 'cabs' and 'caps.' A combination of a base and an alkaline buffer also may be used as the second material. As used in the claims and this specification, the term 'base' includes a base, an alkaline buffer and a combination of one or more bases and alkaline buffers.

The third material contains an effective amount of an appropriate oxidizing agent, such as sodium perborate (NaBO$_3$). A molar concentration in the range of 50 to 2000 mM in the toilet bowl is believed to be effective. Other oxidizers are suitable, such as hydrogen peroxide (H$_2$O$_2$), permanganate, hypochlorite, iodine, sodium percarbonate or potassium percarbonate. The luminol and oxidizer preferably are added to the toilet bowl water in a stochiometric ratio.

After preparing the water, the patient defecates or urinates into the toilet bowl. The chemiluminescent luminol produces a transient bright bluish glow when mixed with an appropriate oxidizing agent in the presence of a catalyst. Red blood cells on the surface of the feces or in the urine will lyse in the hypotonic toilet bowl water containing the luminol and an oxidizer, releasing hemoglobin into the water of the toilet bowl. The released hemoglobin contains iron, which is an effective catalyst for the reaction between the luminol and the oxidizer. If the amount of blood present in the feces or the urine is above the detection limits of the test, the water in the toilet bowl transiently will glow blue.

Residual amounts of household cleaners containing bleach in the toilet bowl water can weakly catalyze the reaction of the luminol and oxidizer, causing some residual background glow. Detection of the transient blue glow that is greater in intensity than the background level is a positive test result indicating the presence of iron and hence blood in the toilet bowl. The transient blue glow and the background glow may be detected either by direct observation by the patient or through use of a detection apparatus, The luminol, oxidizer and base may be dispensed into the toilet bowl in any convenient form, such as by the patient manually adding solid tablets, powders, sachets, aqueous solutions or suspensions containing the luminol, oxidizer and base. The luminol, oxidizer and base may be dispensed by a dispensing apparatus, such as by one or more dispensers located within the tank of the toilet and controlled by a valve, which may be a solenoid valve. The dispensers alternatively may be configured to dispense the luminol, oxidizer and base to any location of the water supply upstream of the toilet bowl. For a dispensing apparatus that dispenses the luminol, base and oxidizer into the toilet tank or to any other upstream location, the toilet should be flushed immediately prior to conducting the test to charge the toilet bowl with water mixed with fresh luminol, base and oxidizer. Providing that the dispensers dispense the luminol, oxidizer and base to the toilet tank or to any other location upstream of the toilet bowl provides for mixing of the luminol, oxidizer and base with the water that will be in the toilet bowl during the test. The dispensing apparatus may dispense the luminol, base and oxidizer directly into the toilet bowl as an alternative to dispensing to the toilet tank or to another location upstream of the toilet bowl.

The dispensing apparatus may be manual or automatic. For example, the dispensing apparatus may dispense the luminol, base and oxidizer when the toilet is flushed, when the lid of the toilet is raised or lowered, when a switch is operated by the patient, or when a conventional proximity detector detects the presence of the patient. The dispensing apparatus may dispense the luminol, oxidizer and base when a sensor detects that a person is sitting on the toilet seat, or by a detector that detects that the person was sitting on the toilet seat but is no longer sitting on the toilet seat. Any apparatus that dispenses the luminol, base and oxidizer into the toilet bowl water prior to the urination or defecation by the patient is suitable.

While the method of the invention may be used to detect blood without a separate apparatus other than the luminol, oxidizer, base and the toilet bowl, an electronic detection apparatus can improve detection accuracy, automatically record results, reduce false positive or negative results, and avoid requiring the patient to physically observe the background light levels or to physically observe the luminol-oxidizer reaction directly. Observing the background light levels or observing the reaction directly by a patient creates the risk of bias on the part of the patient.

The chemiluminescent reaction of the luminol and oxidizer emits light with an emission peak of approximately 450 nm in wavelength. A suitable detection apparatus is configured to detect that wavelength of light. The detector may take any of several configurations. First, the detector may utilize photodiodes configured to respond to all wavelengths of visible light or more narrowly to light of approximately 450 nm in wavelength. Model UVG-20C photodetectors available from International Radiation Detectors, Inc. ('IRD'), of Torrance, Calif. are believed to be suitable when combined with optical filters centered on 450 nm and with a bandwidth of plus or minus 40 nm. Such filters are known in the art.

The photodiodes are operably connected to a power supply and an appropriate amplifier to amplify the signal generated by the photodiodes in response to the light from the luminol. The detection apparatus can be as simple as a an alarm circuit attached to the amplifier and triggered when the signal reaches a pre-determined threshold, indicating the presence of glowing luminol and indicating the presence of iron and hence blood in the toilet bowl.

Alternatively, the detection apparatus may be controlled by a microprocessor. In the instance of the microprocessor-controlled apparatus, the photodetectors are operably connected to the microprocessor and computer memory. Any sensor capable of detecting light of the 450 nm wavelength may be used with the microprocessor and other possible photodetectors include charge-coupled devices or active pixel sensors.

The microprocessor is programmed to determine a baseline level of light in the 450 nm range of the prepared water in the toilet bowl after luminol, oxidizer and base are added, but before the patient defecates or urinates in the toilet bowl water.

For example, the patient may power up the detection apparatus and sit on the toilet seat. The apparatus dispenses the luminol, base and oxidizer into the toilet tank and causes the toilet to flush, filling the toilet bowl with prepared water. Once the apparatus is powered on, the microprocessor receives photodetector signals from the photodetectors continuously. The photodetector signals correspond to the brightness of the light detected by the photodetector in the range of wavelengths emitted by the luminol-oxidizer reaction.

The microprocessor determines that the signals from the photodetectors received early in the test sequence at a first time are background signals. The background signal, also referred to herein as 'baseline' signals, preferably are determined after the patient sits on the toilet seat. Since there should be no blood in the stools of a normal patient, the intensity of 450 nm light detected by the photodiodes should remain at the level of the background signals and should not increase over the course of the test.

The microprocessor compares the detected light levels of the baseline signals to sample signals from the photodetector at a second time. The second time is after the first time and the microprocessor infers that urine or feces are present in the toilet bowl. The microprocessor determines whether the photodetector signals and hence the light levels vary from the baseline by a significant amount during the course of the test and thus whether iron from hemoglobin is catalyzing the luminol-oxidizer reaction.

The microprocessor records the results to the computer memory and displays the results to the patient. If the microprocessor determines that the light levels in the 450 nm range is increased significantly above background the microprocessor may provide an alert to the patient, such as a visual or audible alarm. The microprocessor may determine whether the sample signal exceeds the background signal by any of a plurality of graduated increments. A display may indicate any light intensity above background with increasing number of bars up to a pre-determined maximum, such as five bars, similar to the signal indicator of a cellular telephone. The display may comprise a number of lamps, such as four LED lamps, and may indicate light intensity above background by illuminating a number of lamps corresponding to the detected light intensity above background.

Where the second material includes both luminol and one or more fluorophores, the fluorophore may emit light of a different wavelength than the luminol. In the case of fluorescein, the wavelength of maximum emissions in water is 521 nm. The use of a fluorophore may allow the wavelength of the light emitted in the toilet bowl to be tailored to the wavelength of maximum sensitivity of the detector. The fluorophore also my emit more light than luminol alone, easing the task of detecting the light. Use of fluorophore(s) also may help to screen out background light by providing two or more different wavelengths of light to detect; for example, if luminol and fluorescein are present and the detector detects light at 450 nm (corresponding to light emitted by luminol) and at 521 nm (corresponding to light emitted by fluorescein), but detects less light intermediate to those two wavelengths, then the detector may conclude that the light emitted in the toilet bowl exceeds the background light. Use of multiple fluorophores may allow the emitted wavelength to be further shifted to match a detector or to make detected light more visible, as when light emitted by one fluorophore at a first wavelength causes a second fluorophore to emit light at a second wavelength, where the light at the second wavelength is easier to detect by the detector or easier to see by a human being.

One advantage of the method and apparatus of the invention is that rather than collecting a single snap-shot sample every few years, the test may be repeated with each bowel movement or for more extended periods, e.g. weekly, and the detection apparatus may readily collect the results of a large number of sampling events. The detection apparatus may be programmed to compare the samples to each other and to conduct statistical analysis of the results. If the detection apparatus determines that a statistically significant number of sample results indicate blood in the stool or urine, the detection apparatus may alert the patient. The analysis of the large number of sample results may correct for false positives that may result from menstrual blood, colitis, hemorrhoids, or dietary changes.

The detection apparatus may feature a photodetector having one or more photodiodes and accompanying amplifiers that may be incorporated into the seat of the toilet bowl. The photodiodes may be embedded in the bottom of the toilet seat or the toilet lid and facing the water in the toilet bowl. The microprocessor and other electronics may be incorporated into the toilet seat or lid or may be housed in a separate enclosure remote from the toilet seat but operably connected to the photodetector. The separate enclosure may include a display to advise the patient of the status of the device, to allow the patient to turn the device on and off, and to display the intensity of the detected light or otherwise to inform the patient of the results of the blood detection operation. The enclosure may be a small box similar in size to a cell phone housing. The device may be DC powered and may feature batteries or an external power supply. The detection apparatus may utilize any other form factor and any other location that allows the photodetectors to detect the light emitted from the hemoglobin-oxidizer-luminol reaction in the toilet bowl. The detection apparatus may be separate from the toilet seat. The detection apparatus may be a stand-alone device that is supported by the toilet bowl. Alternatively, the detection apparatus may be incorporated into the toilet bowl itself.

In practice, the inventors have discovered that the luminol-oxidizer reaction catalyzed by iron in blood in the toilet bowl is readily detectable using directional photodiodes directed downward toward the water in the toilet bowl from the underside of the toilet seat or lid, and operated during a time when the lid is closed. Using this arrangement, measurement of background light levels has been unnecessary and use of fluorophores also has been unnecessary. The inventors believe that detection and measurement of background light levels and use of fluorophores may increase the sensitivity of the apparatus and method. The inventors believe that the arrangement of this paragraph will work if the entry of ambient light into the toilet bowl is partially blocked by the patient on the toilet rather than by the lid and believe that the luminol, oxidizer and base can be added either before or after the patient urinates or defecates and either by a dispenser or manually by the patient.

The patient may transport the collected data to the patient's physician for evaluation. The patient physically may transport the separate enclosure or may transport a separate computer memory, such as a flash drive. The patient may transmit the data to the physician electronically, as by an attachment to an e-mail message or over the Internet. The detection apparatus may be attached to a network such as a local area network, a wide area network, the Internet or a wireless communication system. The apparatus may communicate with the physician over the communication network without intervention from the patient. The physician may evaluate the results and determine whether further testing or intervention is appropriate for the patient.

The apparatus may take the form of an appropriately programmed handheld computing device, such as a 'smart phone.' To use the handheld computing device embodiment, and after adding luminol and oxidizer to the toilet bowl, the patient will start a dedicated software application resident on computer memory of the handheld computing device and will take a first photograph of the toilet bowl prior to urinating and/or defecting using the built-in camera of the handheld device. The application programs the handheld device to electronically filter the detected light of the first photograph to determine the intensity of light at the 450 nm wavelength. The handheld computing device records the light level detected at 450 nm in the first photograph as the background. After defecation and/or urination, the patient then takes a second photograph of the toilet bowl. The handheld computing device electronically filters the light recorded in the second photograph to determine the light level at the 450 nm wavelength. The device will compare the 450 nm light intensity detected in the second photograph to that of the background. The handheld computing device is programmed to record the results to computer memory and to erase both photographs. The handheld computing device can be programmed to communicate the results over the cellular telephone system to a computer, such as a computer operated by the patient's physician.

The screening apparatus and method described above requires no handling of feces or urine. It is safe and inexpensive and can be used frequently, unlike the current screening paradigms. The ease and privacy of use will encourage patient compliance.

IV. BRIEF DESCRIPTION OF THE DRAWINGS

Figure 2:
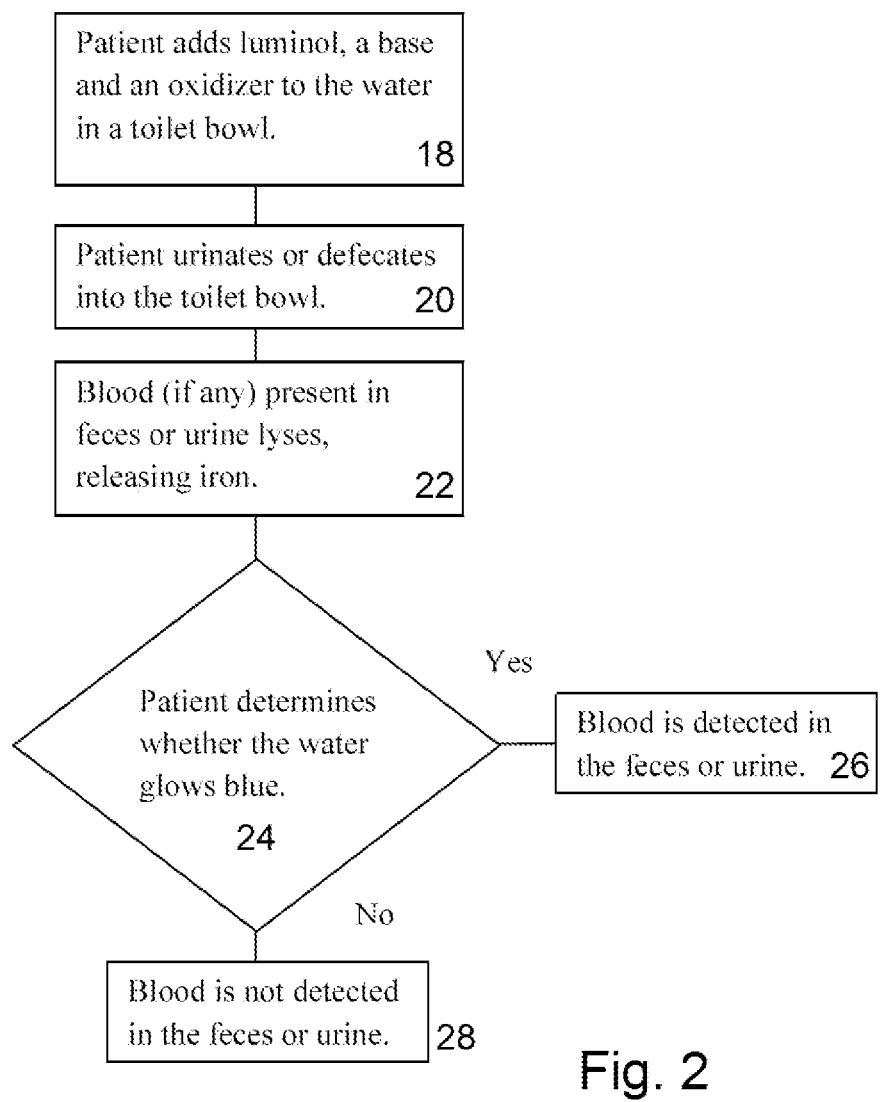
Figure 3:
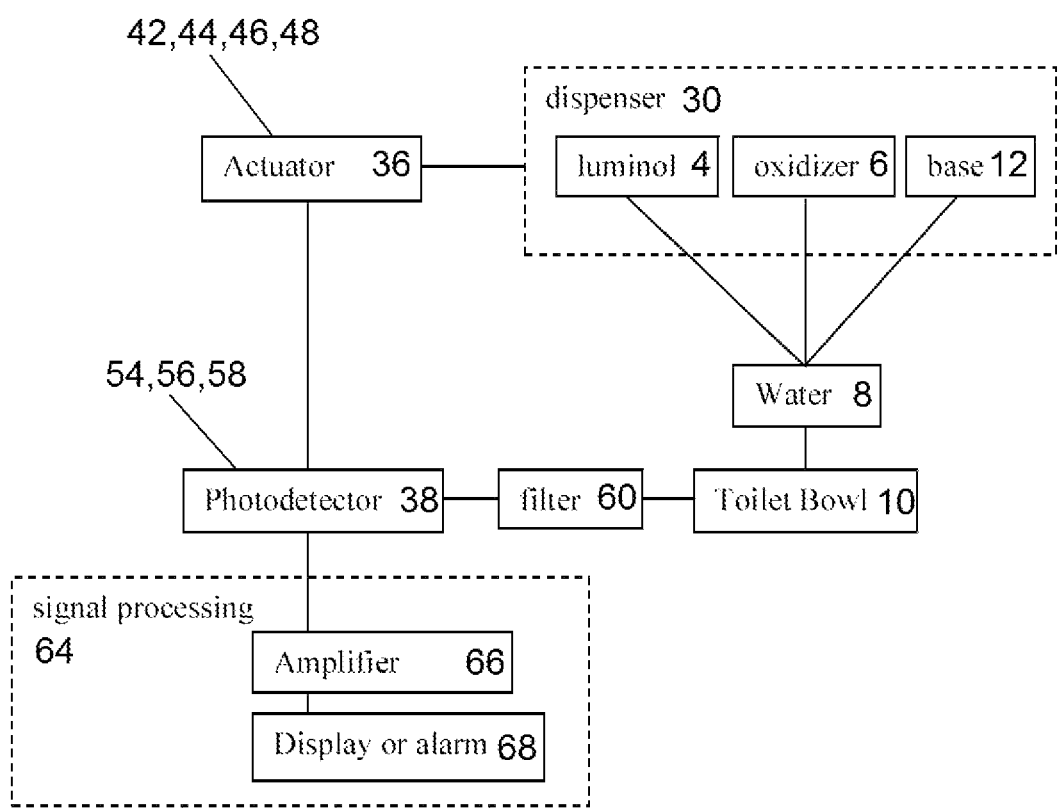
Figure 4:
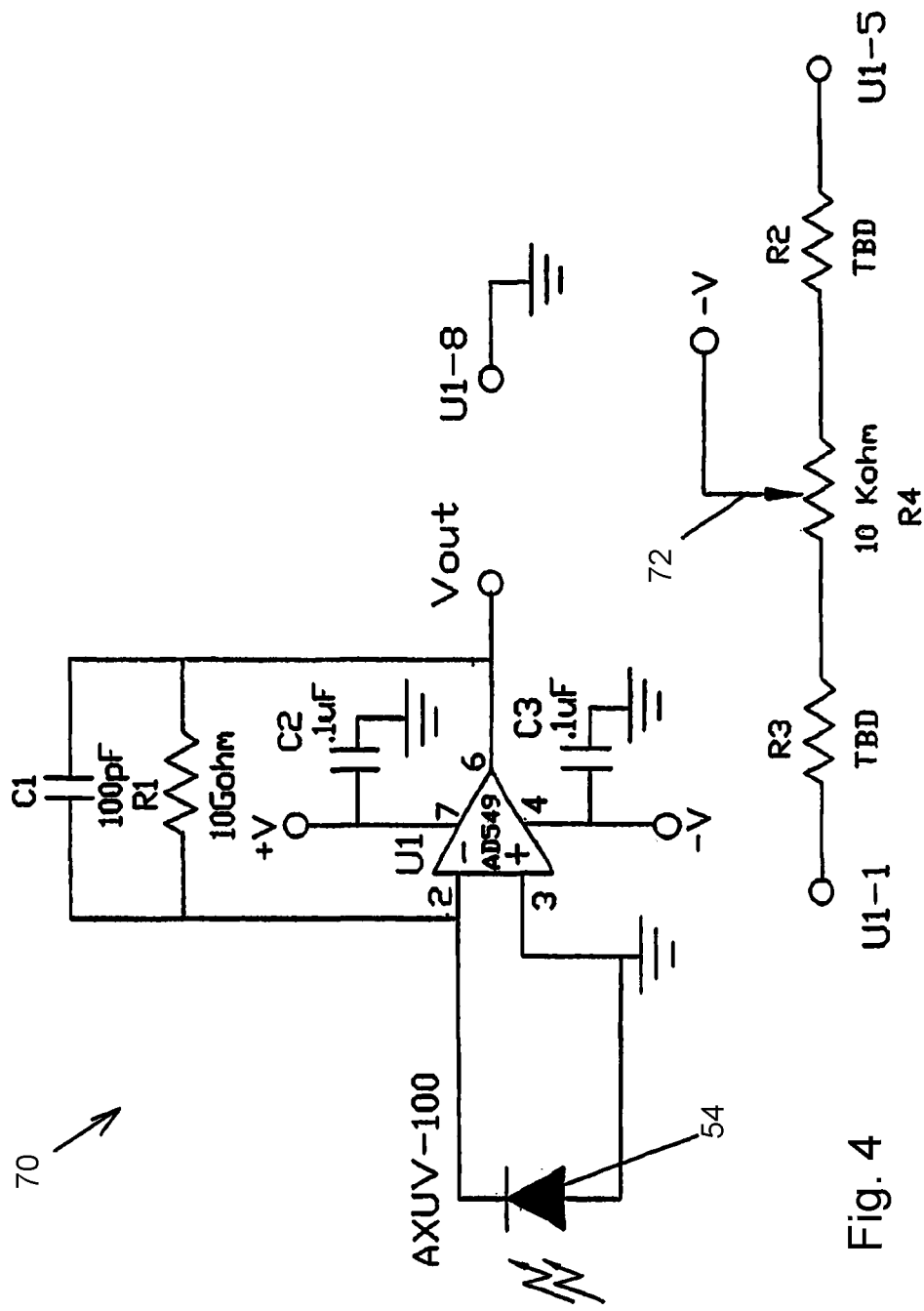
Figure 5:
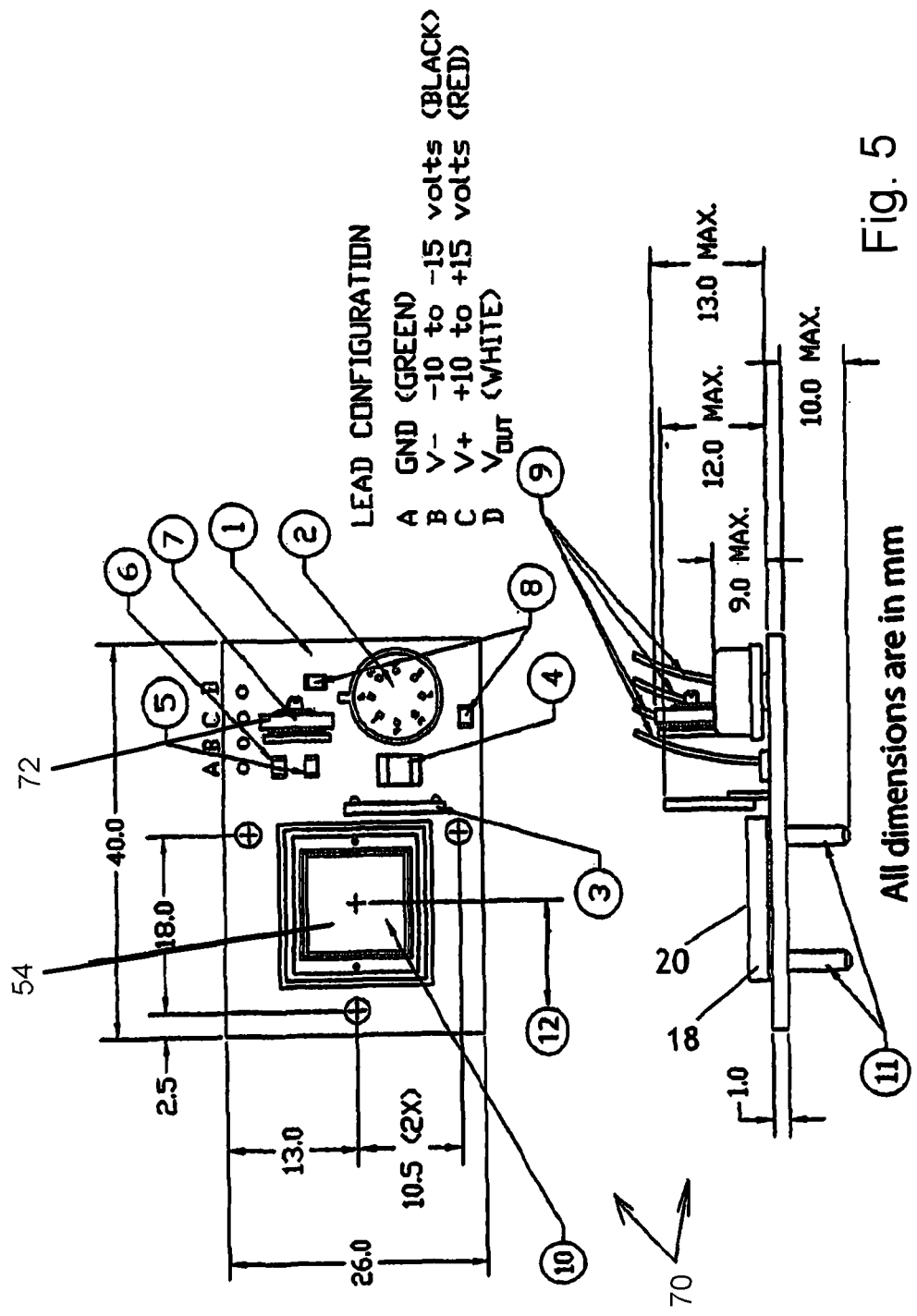
Figure 7:
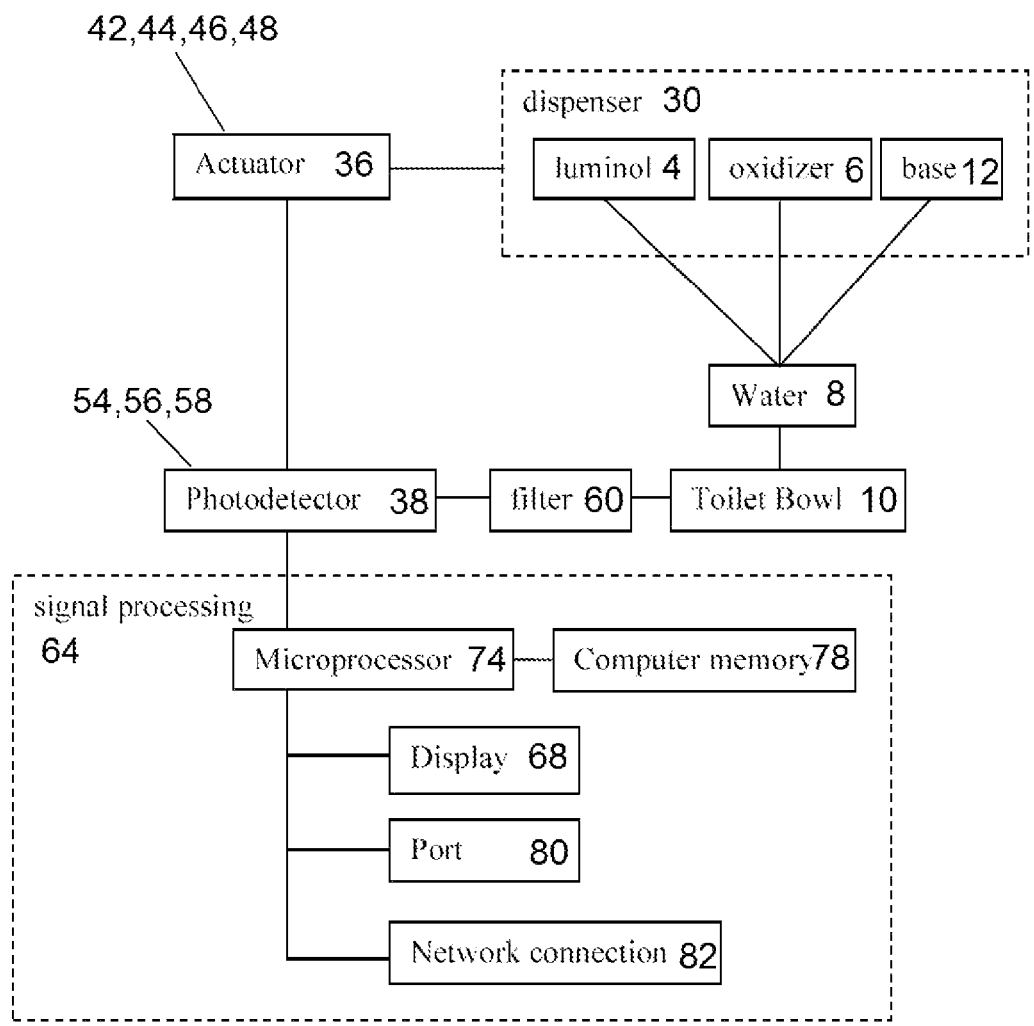
Figure 8:
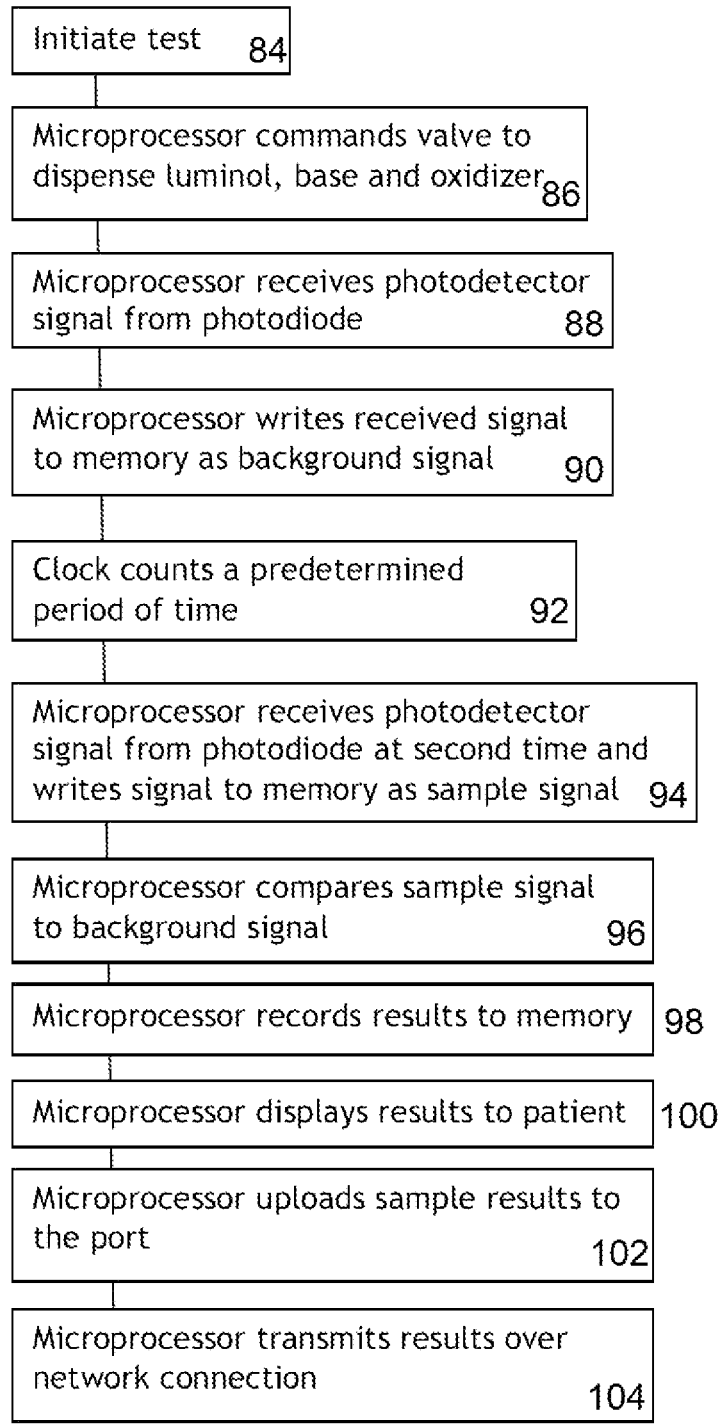
Figure 9:
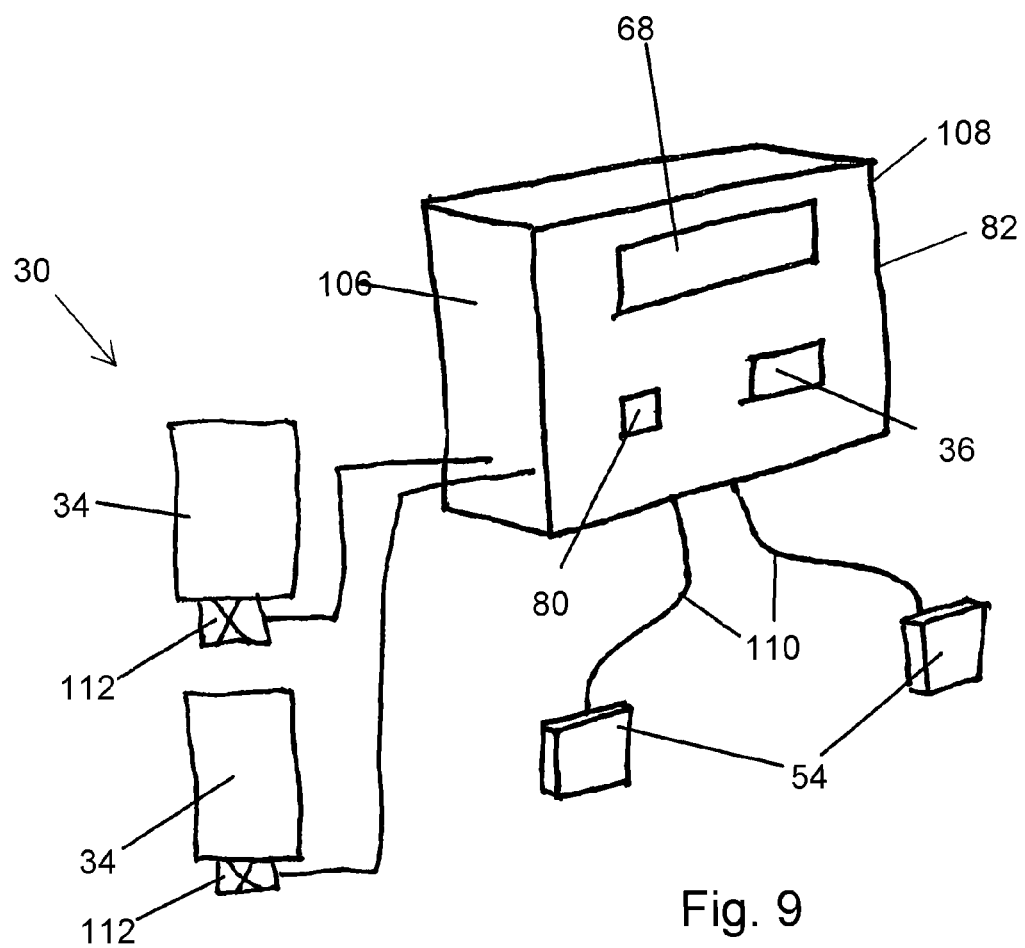
Figure 10:
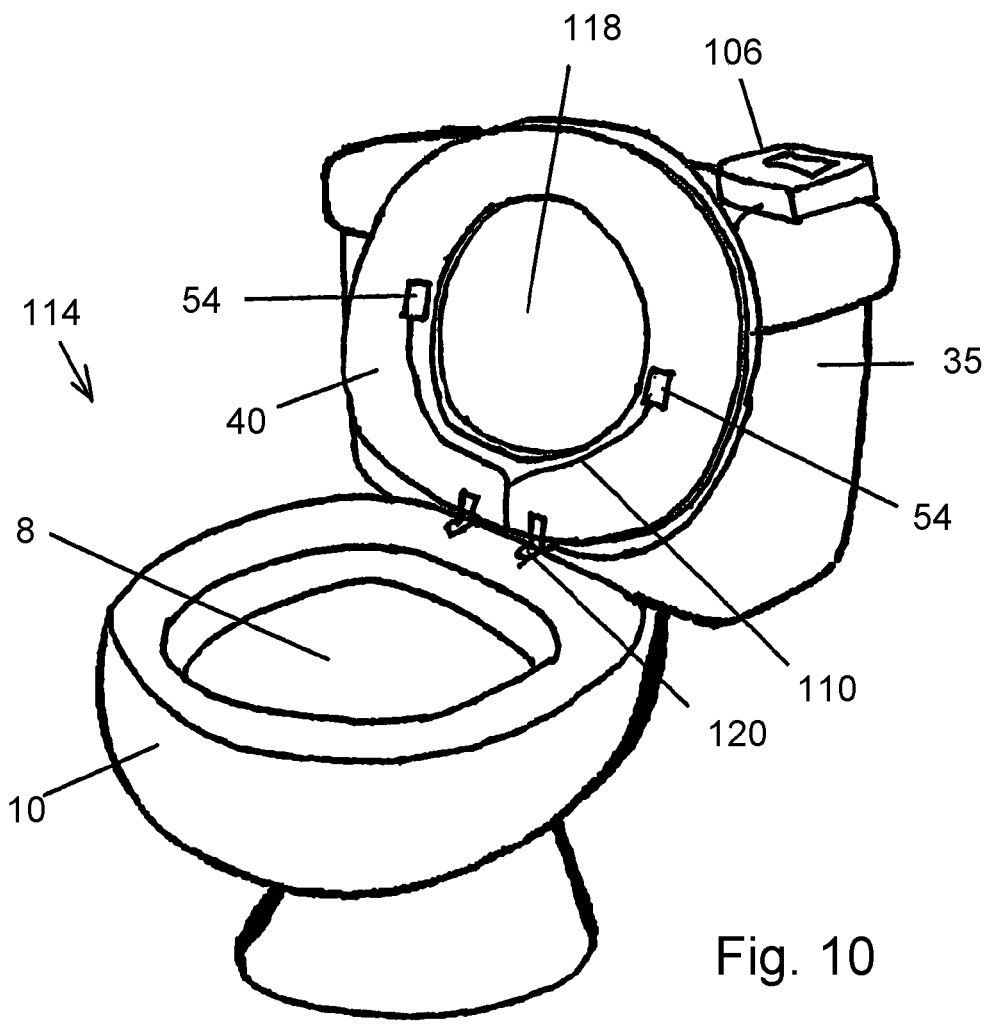
Figure 11:
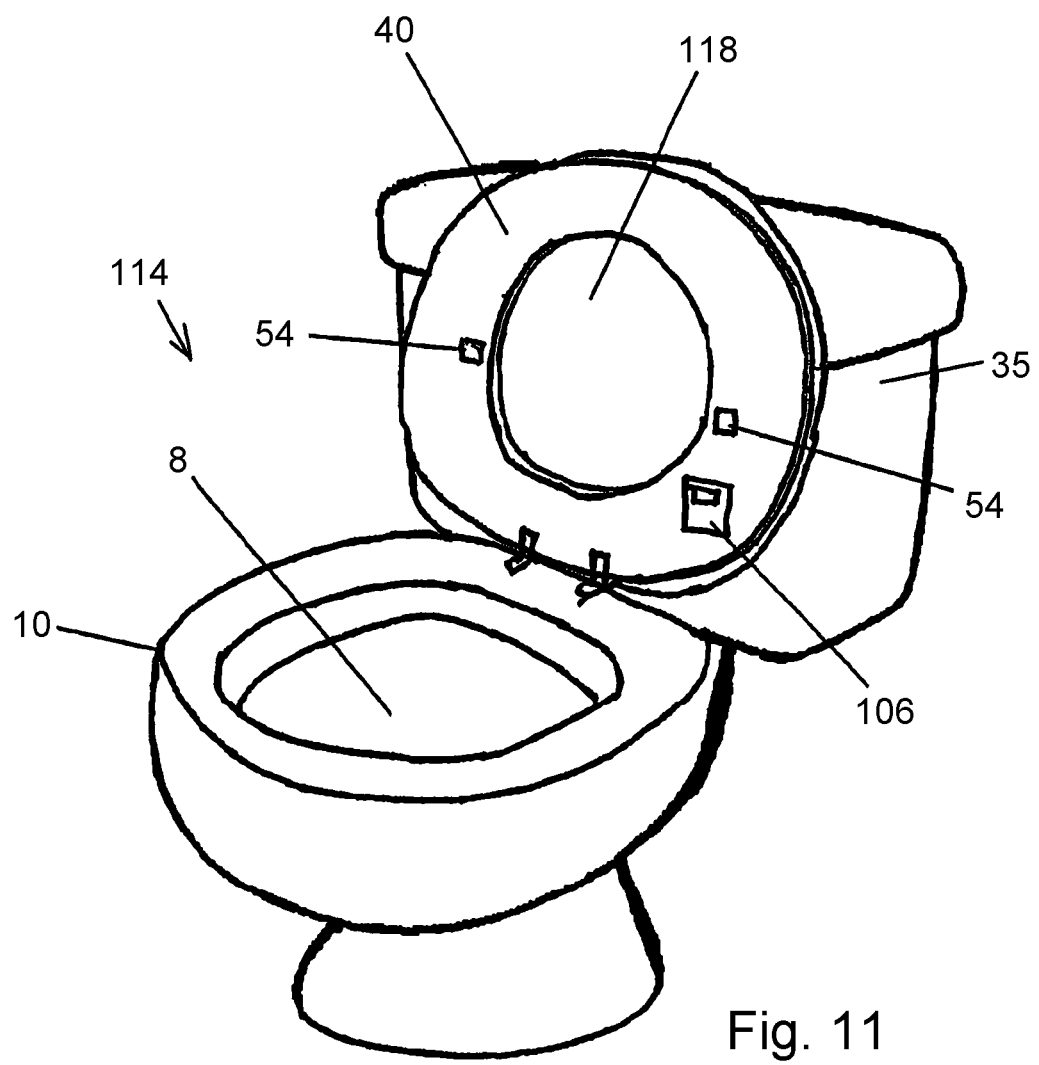
Figure 12:
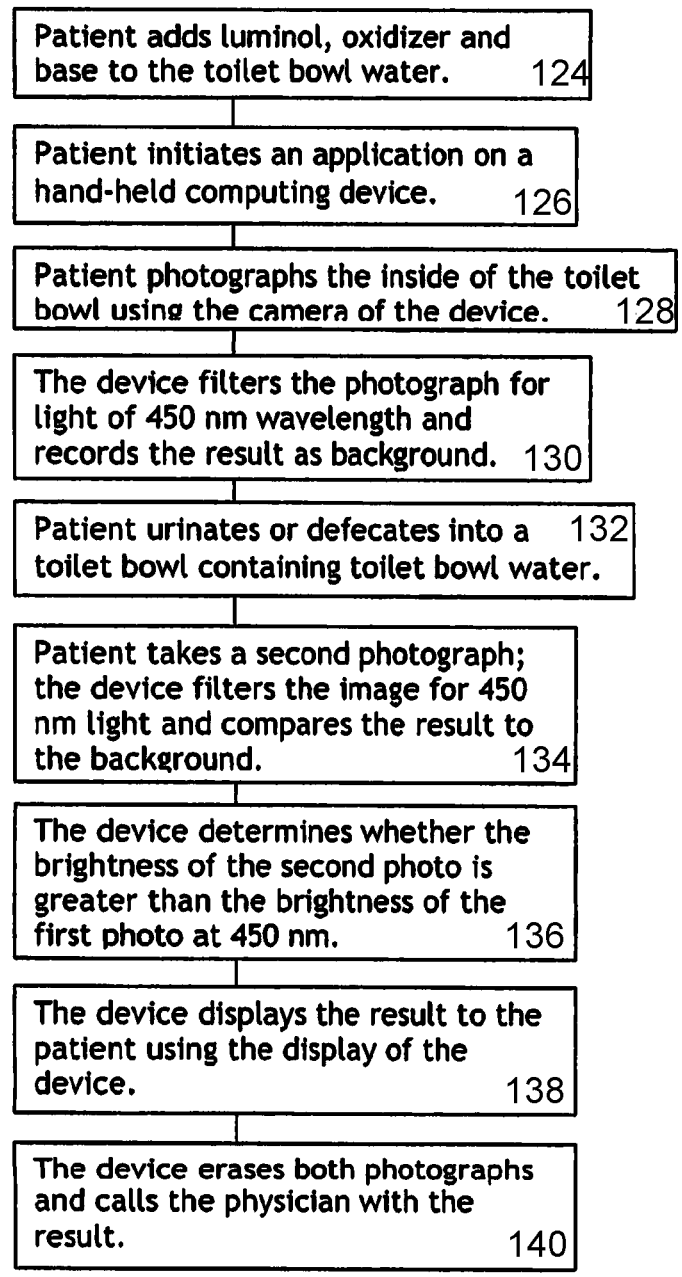

FIG. 1 is a diagram of the luminol-oxidizer reaction.
FIG. 2 is a flow chart of one method of the invention.
FIG. 3 is a schematic diagram of an embodiment of the apparatus.
FIG. 4 is a circuit diagram of a simple detector circuit.
FIG. 5 is a plan and a side view of the detector of FIG. 4.
FIG. 6 is a parts list for the detector circuit of FIG. 4.
FIG. 7 is a schematic diagram of a microprocessor-implemented detection apparatus.
FIG. 8 is a flow chart of information flow through the apparatus of FIG. 7.
FIG. 9 is a schematic diagram of a detection apparatus.
FIG. 10 is perspective view of a first embodiment of the apparatus on a toilet.
FIG. 11 is a perspective view of a second embodiment of the apparatus on a toilet.
FIG. 12 is a flow chart of an application for a hand-held detection apparatus.
FIG. 13A-13D is a circuit diagram for a detection apparatus configured to detect different amounts of light.
FIG. 14A-F is a circuit diagram for a another embodiment of the detection apparatus configured to detect different amounts of light.
FIG. 15 is method from the point of view of an equipment supplier or manufacturer.

V. DESCRIPTION OF AN EMBODIMENT

The method and apparatus is for the screening of feces and urine for blood in a toilet bowl 10. As shown by FIG. 1, the apparatus and method of the invention utilize the reaction 2 of luminol 4 with an oxidizer 6 in alkaline conditions in water 8 in a toilet bowl 10. In the diagram of FIG. 1, the oxidizer 6 is hydrogen peroxide; however, several different oxidizers 6 are suitable, as described above. The alkaline conditions are achieved in the water 8 in the toilet bowl 10 by the addition of a base 12, such as sodium borate. Other bases 12 also are suitable to achieve the needed alkaline conditions. The reaction between the luminol 4 and the oxidizer 6 is slow unless the reaction is catalyzed, as by the iron 14 contained within the hemoglobin in red blood cells. The reaction is rapid in adequately basic conditions and in the presence of iron 14, resulting in the characteristic blue glow of light 16 from the reacting luminol 4 in the presence of blood.

The simplest form of the method is illustrated by FIG. 2.

In the first step 18 of FIG. 2, the patient prepares the water 8 in the toilet bowl 10 by adding luminol 4, the base 12 and the oxidizer 6 to the water 8. In the second step 20 of the method, the patient urinates or has a bowel movement, or both, into a toilet bowl 10. In the third step 22 of FIG. 2, the difference in osmolarity between the water 8 of the toilet bowl 10 and the contents of any red blood cells in the feces or urine in the toilet bowl 10 cause the red blood cells to lyse. The lysis of the red blood cells causes the red blood cells to release their contents into the water 8 of the toilet bowl 10. The released contents include hemoglobin, which contains iron 14. If blood is present, the reaction between the luminol 4 and the oxidizer 6, catalyzed by the iron 14 from the hemoglobin, causes the water 8 of the toilet bowl 10 to glow blue.

In the fourth step 24 of FIG. 2, the patient observes the water 8 of the toilet bowl 10 and determines whether the toilet bowl 10 water 8 is glowing blue. If the water 8 glows blue, then the results of the method are positive and the patient likely has blood in his or her bowel movement or urine. The blue glow may be caused by the presence of materials other than blood, such as copper or bleach. The patient may consult with his or her physician to determine whether the positive test should be followed with other tests to confirm the presence of the blood, determine the source of the blood and treat the cause of the bleeding. From step 28, if the patient does not observe a blue glow, then blood is not detected.

The invention may include a detection apparatus that may be simple or complex. FIGS. 3 through 6 illustrate a detection apparatus that utilizes a dispenser 30 to dispense the luminol 4, oxidizer 6 and base 12 into the water 8. The luminol 4, oxidizer 6 and base 12 may take the form of solid tablets. The luminol 4 and the base 12 may be formed into one tablet, while the oxidizer is formed into a second tablet. The luminol 4, oxidizer 6 and base 12 alternatively may be in the form of sachets, powders, solutions or suspensions 32. The luminol 4, oxidizer 6 and base 12 may be stored in reservoirs 34, as reservoirs 34 in or defined by the toilet tank 35, all shown by FIG. 7. The luminol 4 may include one or more fluorophores.

In the apparatus of FIG. 3, an actuator 36 is operably connected to the dispenser 30. The actuator 36 is operably connected to the dispenser 30 and also connected to the photodetector 38. The actuator 36 may be a manually-operated control, such as a button, a touch screen, a dial, a series of buttons, or any other controls known in the art. The actuator 36 may be an automatic control, such as a pressure switch, configured to detect the presence or absence of the patient on a toilet seat 40. The actuator 36 may be configured to detect the position of the toilet seat 40 or to detect a change in position of the toilet seat 40. The actuator 36 may be configured to detect the proximity of the patient.

The actuator 36, when actuated by the patient, activates effectors 42, such as solenoid valves, to dispense the luminol 4, oxidizer 6 and base 12 into the toilet bowl 10. The actuator 36 may be in the form of a familiar lever flushing actuator 44, such as the flushing levers present on prior art flush toilets 8. The effector 50 may be configured to flush the toilet 8, recharging the toilet bowl 8 with water 10. As the toilet bowl 10 refills, the dispenser 30 charges the incoming water with luminol 4, oxidizer 6 and base 12.

From FIG. 3, the actuator 36 also activates the photodetector 38. The photodetector 38 may be one or more photodiodes 54. Alternatively, the photodetector 38 may utilize any other technology to detect light 16 emitted by reacting luminol 4 and oxidizer 6, such as charge-coupled devices 56 or active pixel sensors 58.

The photodetector 38 is configured to detect light 16 of the range of wavelengths of light 16 emitted by the reaction 2 within the toilet bowl 10. The photodetector 38 is selected to be sensitive to about a 450 nm wavelength, which is believed to be the wavelength of the light 16 emitted by the luminol-oxidizer reaction 2. Where the photodetector 38 is composed of photodiodes 46, photodiodes 46 may be equipped with filters 60 to limit the light 16 reaching the photodiodes 46. A bandpass optical filter 60 having a range of wavelengths 62 of 450 nm+/−40 nm, or 410 nm to 490 nm, is believed to be suitable. Where one or more fluorophores are used, the photodetector 38 may be selected to be sensitive to light emitted by the one or more fluorophores. Photodetector 38 may be sensitive to two or more ranges of wavelengths, as where the photodetector is sensitive to the range of wavelengths emitted by the luminol-oxidizer reaction 2 and to a range of wavelengths emitted by a fluorophore when exposed to light from the luminol-oxidizer reaction 2 or light from another fluorophore.

In the relatively uncomplicated apparatus of FIG. 3, the photodetector 38 is a photodiode 54 and is attached to a signal processing module 64 comprising an amplifier 66 and a display or alarm 68.

An amplifier circuit 70 amplifies the signal from one or more photodiodes 46. A plan and side view of the amplifier circuit 70 of FIG. 4 is illustrated by FIG. 5. The photodiode 54 is equipped with an optical filter 60, as discussed above. A parts list for the amplifier of FIGS. 4 and 5 is included as FIG. 6. The output of the amplifier 70 can operate a lamp or audible alarm when the detected light 16 in the 450 nm range reaches an alarm threshold to alert the patient. The simple amplifier circuit of FIGS. 4 through 6 does not consider the baseline for ambient light 16 in the 450 nm range; however, the alarm threshold of the apparatus may be adjusted with potentiometer 72. A simple photodetector 38, such as that illustrated by FIGS. 4 and 5, may be used without a dispenser, in which case the patient manually adds the luminol 4, oxidizer 6 and base 12 to the water 8.

FIGS. 7 through 11 illustrate a more complex detection apparatus. From the schematic diagram of FIG. 7, a photodetector 38 includes a photodiode 54 configured to detect light 16 in the 450 nm range, +/−40 nm, as by a band pass filter 60. The photodetector 38 generates a photodetector signal 76 in response to the 450 nm range light 16 detected by the photodiode. The photodetector signal has a value, and the magnitude of the value of the photodetector signal is determined by the brightness, duration, or both of the light 16 impinging upon the photodiode 54. The photodetector 38 is operably connected to a microprocessor 74. Microprocessor 74 is also connected to computer memory 78, display 68, port 80 and network connection 82. Programs to operate the apparatus are stored in computer memory 78, which also is configured to store data in response to a command from the microprocessor 74. A power supply provides power to the apparatus, which may be powered by batteries or by line power. The microprocessor 74 is configured to display the results on a display 68. The data stored in computer memory 78 may be downloaded through port 80. Programs resident in computer memory 78 also may be loaded through port 80.

The operation of the microprocessor-controlled apparatus of FIG. 7 is illustrated by the flow chart of FIG. 8. The microprocessor 74 receives a command from the actuator 36 to initiate a test 84. The microprocessor 74 commands effectors 50 to flush the toilet 10 and to recharge the toilet 10 with water 8. The microprocessor 74 commands (step 86) effectors 50 to open valves, charging the incoming water 8 with luminol 4, oxidizer 6 and base 12. The water 8 is now prepared for the test.

From step 88 of FIG. 8, the photodetector 38 generates a photodetector signal 76 corresponding to the 450 nm range light 16 detected by the photodiode 54 at a 'first time,' prior to defecation or urination by the patient into the toilet bowl 10. In step 90, the microprocessor 74 stores the photodetector signal 76 received at the first time as a background signal to indicate ambient light 16 and any background light 16 from non-hemoglobin catalyzed luminol-oxidizer reaction 2. Recording the background light 16 accounts for any nominal luminol 4 chemiluminescence resulting from household cleaners containing bleach used previously on the toilet bowl 10 or from any other contaminants. In step 92 of FIG. 8, the microprocessor 74 consults a system clock to count a predetermined period of time to allow the patient to urinate or defecate into the toilet bowl 10 and to allow the luminol-oxidizer reaction 2 to occur. At the conclusion of the predetermined period of time, the microprocessor 74 records the photodetector signal 76 as the sample signal 94.

As a first alternative to step 92 of FIG. 8, the microprocessor 74 may wait for a second activation of actuator 36 to receive and record the sample signal 94 from the photodetector 38. As a second alternative to step 92 of FIG. 8, the microprocessor 74 may record the photodetector signal 76 continuously to computer memory 78. The passage of time of step 92, or an activation of actuator 36 by the patient, or the period of time after the first time, or the value of the detected photodetector signal defines the 'second time' at which the sample signal 94 is recorded.

The microprocessor 74 records 94 the photodetector signal 76 from the photodetector 38 received during the 'second time' to computer memory 78 as the 'sample signal.' The sample signal corresponds to the brightness of the light 16 from the toilet bowl 10 detected after the patient urinates or defecates or both in the toilet bowl 10 and as the reaction 2, if any, occurs.

In step 96 of FIG. 8, the microprocessor 74 next compares the sample signal collected at the second time after the patient urinates or defecates into the prepared water 8 to the background signal collected at the first time prior to urination or defecation of the patient. Any increase in light 16 level in the 450 nm range from the first time to the second time is considered as due to the luminol-oxidizer reaction 2 in the toilet bowl 10 water 8. In step 98 of FIG. 8, the microprocessor 74 records the results to computer memory 78.

To reduce false positive results, the microprocessor 74 may be configured to report a positive result only if the sample signal exceeds the background signal by more than a predetermined amount or by a statistically significant amount. The microprocessor may be configured to statistically evaluate a plurality of results of a plurality of sampling events and to report a positive result only if the positive results passes predetermined statistical tests, as are known in the sampling art. The microprocessor 74 may be configured to throw out or otherwise discount results that fall outside of predetermined boundaries; for example, if the photodetector 38 detects an excessive amount of light 16 outside the target wavelength range during the recording of the sample signal, indicating contamination of the sampling signal by ambient light 16.

As indicated by step 100 of FIG. 8, if the detection apparatus is equipped with a display 68, the microprocessor 74 may cause the results to be displayed to the patient. The microprocessor 74 may be configured to make a binary determination of whether blood is present or not present and to communicate that yes-or-no determination to the patient.

The microprocessor 74 may be configured to make not only the binary determination of whether an increase in light 16 due to the luminol-oxidizer reaction 2 occurs, but also to detect graduated differences in brightness due to the luminol-oxidizer reaction 2. The differences in brightness may correspond to different amounts of blood present in the urine or feces. In such a configuration, the microprocessor 74 determines whether the light 16 recorded at the second time in the sample signal is greater in brightness than the background signal to a detection threshold and also to compare the brightness of the detected change in light 16 above the detection threshold to a reference standard. The microprocessor 74 is configured to display to the patient using the display 68 whether none, a little or a lot of blood is present. The microprocessor 74 may be configured to display the results as a series of graduated increments to the patient. The graduated increment display may take the form of parallel bars, as are commonly used to indicate wireless telephone signal strength. The graduated increment display may take the form of a series of LED lamps, as illustrated by FIGS. 13 and 14. If the results are positive for blood in the toilet bowl 10 water 8, the patient may consult his or her physician to determine whether additional action is appropriate.

The patient may carry the detection apparatus to his or her physician, who may attach the apparatus 106 to a computer through the port 80. In step 102 of FIG. 8, the microprocessor may allow access by the physician's computer to the background signals and sampling signals from the computer memory 78 through port 80. Alternatively, the patient may load the background signals and sampling signals to an external computer memory, such as a flash drive, and transport the external memory to the physician physically. As shown by step 104, the microprocessor 74 may access the network connection 82 to communicate the results over the network, such as a local area network, a wide area network, the Internet or a wireless communications network, to the patient, physician, other health care provider or other designated person.

As a simplified alternative to the method of FIG. 8, steps 90 through 96 may be eliminated. Either before or after the patient urinates or defecates in the toilet bowl 10, from step 86 the microprocessor 74 commands the apparatus to dispense luminol 4, the base 12 and the oxidizer 6. The toilet lid 118 is closed and directional photodiodes 54 located on the underside of the toilet lid 118 or otherwise directed into the toilet bowl 10 generate a signal corresponding to light 16 detected from luminol-oxidizer reaction 2 in the toilet bowl 10. The microprocessor 74 records the results, as indicated by step 98. The microprocessor also may take steps 100 through 104, as discussed above.

As a second simplified alternative to the method of FIG. 8, step 86 and steps 90 through 96 are eliminated. Either before or after the patient urinates or defecates in the toilet bowl 10, the patient manually adds luminol 4, the base 12 and the oxidizer 6 to water 8 in the toilet bowl 10. The toilet lid 118 is closed and directional photodiodes 54 located on the underside of the toilet lid 118 or otherwise directed into the toilet bowl 10 generate a signal corresponding to light 16 detected from the toilet bowl 10. The microprocessor 74 records the results, as indicated by step 98. The microprocessor 74 also may take steps 100 through 104, as discussed above.

As a third simplified alternative to the method of FIG. 8, either before or after the patient defecates or urinates in the toilet bowl 10, the patient manually adds luminol 4, the base 12 and the oxidizer 6 to the water 8 in the toilet bowl 10. The toilet lid 118 is closed and directional photodiodes 54 located on the underside of the toilet lid 118 or otherwise directed into the toilet bowl 10 generate a signal based on the light detected from the toilet bowl 10. An amplifier 66 amplifies the signal and a display or alarm 68, such as a group of graduated lights, displays the results to the patient.

FIGS. 9-11 illustrate embodiments of the apparatus of the invention. FIG. 9 illustrates one embodiment of the detection apparatus. Enclosure 106 houses the power supply 108, microprocessor 74, computer memory 78, display 68, port 80 and network connection 82. The photodiodes 54 are connected to the microprocessor 74 by wires 110. The port 80 appears on the enclosure 106. The enclosure 106 includes the display 68. The enclosure 106 includes actuator 36. Actuator 36 is operably connected to microprocessor 74. Actuator 36 may be a button, a touch screen, a dial, a series of buttons, or any other controls known in the art. When the actuator 36 is activated for a first time during a testing event, activation of the actuator 36 initiates step 84 of FIG. 8 and the sequence of events indicated by FIG. 8. Dispenser 30 includes reservoirs 34 contained within the toilet tank 35. One reservoir 34 contains luminol 4 and base 12 and the other reservoir 34 contains oxidizer 6. Reservoirs 34 are equipped with valves 112, which may be solenoid valves, and which are operably connected to the microprocessor 74. Dispenser 30 allow one or all of the luminol 4, oxidizer 6 and base 12 to be added to the toilet tank 35, and hence to the toilet water 8, by the apparatus, either on the command of the patient or automatically. Alternatively, reservoirs 34 may be located to dispense the luminol 4, oxidizer 6 and base 12 directly to the water 8 in the toilet bowl 10.

FIG. 10 shows the apparatus of FIG. 9 installed on a toilet 114. The toilet 114 has a bowl 10 that contains water 8. The toilet 114 features a seat 40 and a lid 118. Seat 40 and lid 118 each rotates about hinge 120 between an open and a closed position. Photodetector 38, which may be a pair of photodiodes 54, is mounted to the underside 122 of the toilet seat 40. The photodiodes 54 are configured to receive light 16 from the direction of the toilet bowl 10 when the toilet seat 40 is in the closed position. Photodiodes 54 are connected by wire 110 to microprocessor 74 housed in enclosure 106. Enclosure 106 also contains the power supply 108, computer memory 78, display 68 and port 80. Enclosure 106 may be placed in any convenient location, such as on top of the tank 35 of the toilet 114 or such as on a table or cabinet.

FIG. 11 illustrates an alternative embodiment in which photodiodes 54 and enclosure 106 are incorporated into the toilet seat 40. In the embodiment of FIG. 11, all of the components of the apparatus illustrated by FIG. 9 are incorporated into the toilet seat 40. The photodetector 38 alternatively may be attached to or incorporated into toilet lid 118.

The detection apparatus may not be mounted to the toilet 114 and may instead be a handheld computing device, such as a 'smart phone.' FIG. 12 illustrates a method of the invention utilizing a hand-held computing device. As indicated by step 124, the patient begins the test by preparing the water 8 in the toilet bowl 10 by adding luminol 4, oxidizer 6 and base 12. The patient next initiates an application of the hand-held computing device, as indicated by step 126. The application is a program stored in device memory and running on the microprocessor of the hand-held device. Alternatively, the program may be stored on a server computer and may be downloaded over a computer network by the hand-held device each time the application is run.

On prompting by the device and as indicated by step 128 of FIG. 12, the patient uses the camera built into the hand-held device to take a photograph of the inside of the toilet bowl 10 at the 'first time.' The photograph taken at the 'first time' indicates the light 16 conditions of the toilet bowl 10 after adding the luminol 4, oxidizer 6 and base 12 and prior to urinating or defecating in the toilet bowl 10. The hand-held device analyzes the photograph by electronically filtering the detected light 16 for light 16 of the 450 nm wavelength using conventional techniques. The hand-held device stores a value of the brightness of the light 16 detected at the 450 nm wavelength at the first time as the 'background signal,' as indicated by step 130 of FIG. 12.

As indicated by step 132 of FIG. 12, the patient urinates or defecates into the toilet bowl 10 containing toilet bowl 10 water 8. On prompting by the hand-held device, the patient takes a second photograph of the inside of the toilet bowl 10 at a second time, indicated as step 134. The hand-held device filters the photograph taken at the second time for light 16 in the 450 nm wavelength. The second photograph may be a video having a duration and the second time may extend for that duration. The microprocessor of the hand-held device compares the light 16 of 450 nm in wavelength at the second time to the light 16 detected at the first time. As indicated by step 136, the hand-held device determines whether the light 16 at the second time is brighter than the light 16 at the first time. If the hand-held device detects more light 16 at the 450 nm wavelength at the second time, the device concludes that blood is present in the toilet bowl 10. The handheld device reports the results to the patient, indicated by step 138 of FIG. 13. The hand-held device then may erase both photographs. Optionally, the device may telephone or e-mail the patient's physician with the result, as indicated by element 140 of FIG. 12. The handheld device may take video rather than still photographs. The handheld device also may collect the image data at the first and second times without recording or displaying the data as photographs or video.

Figure 13A:
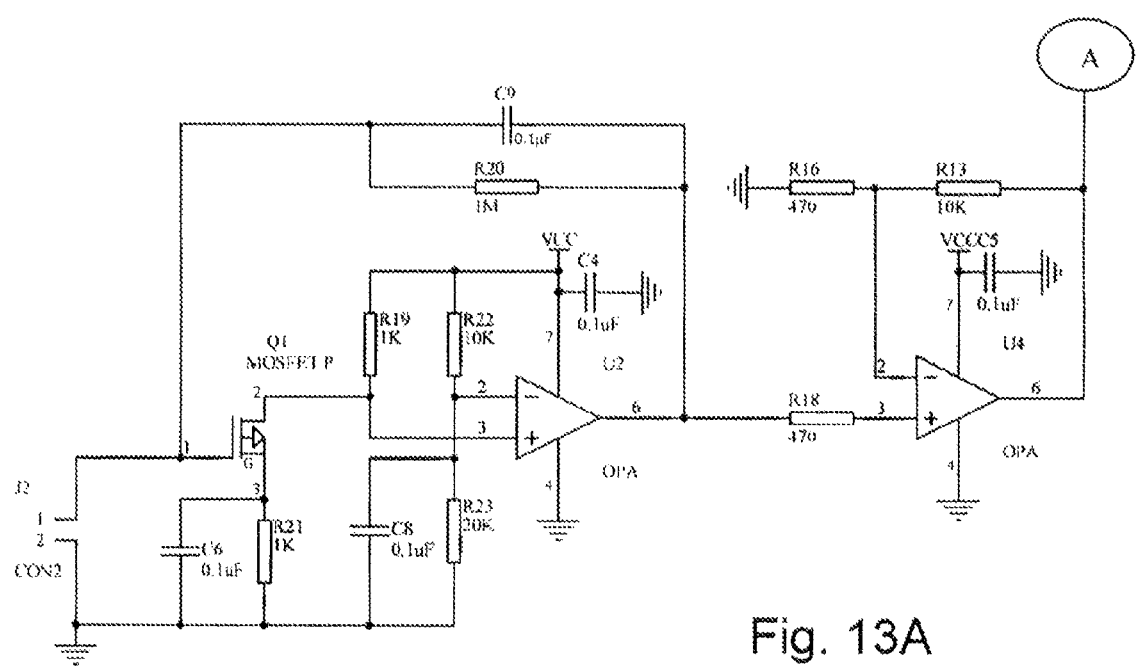
Figure 13B:
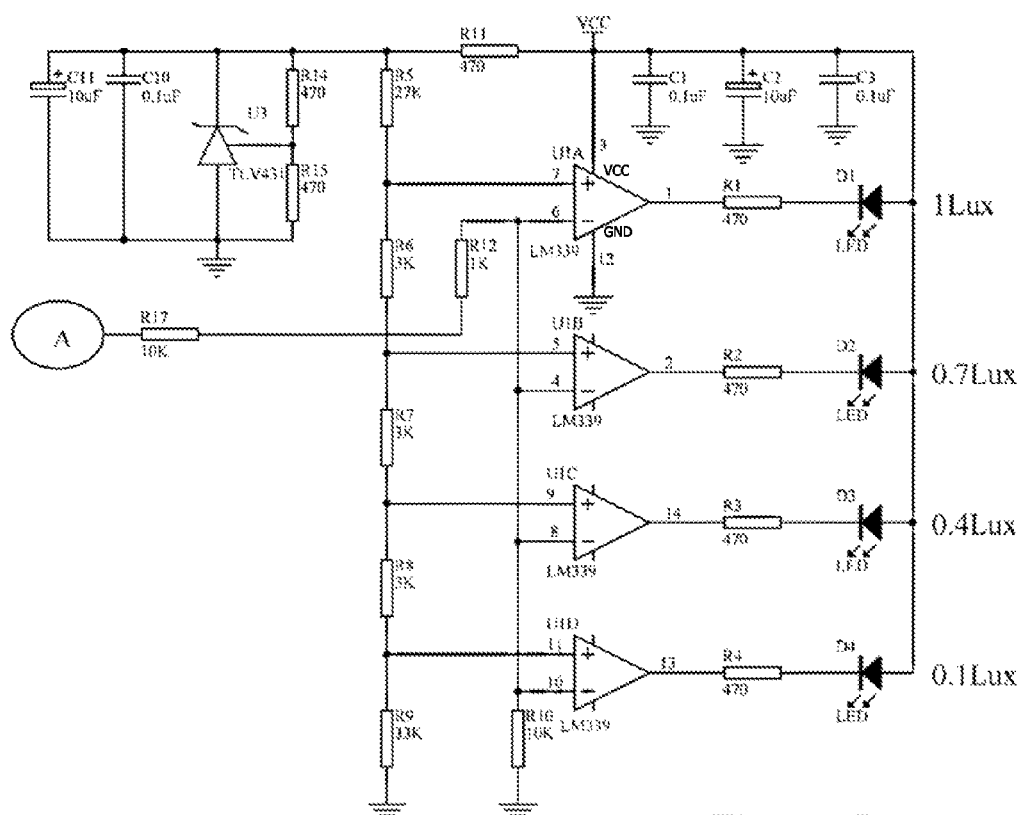
Figure 13C:
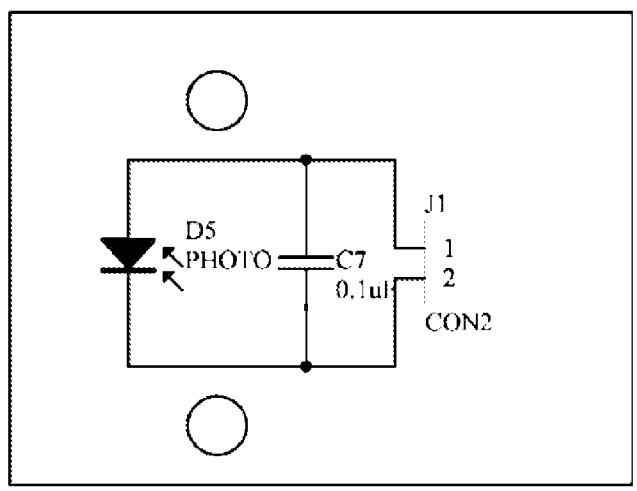
Figure 13D:
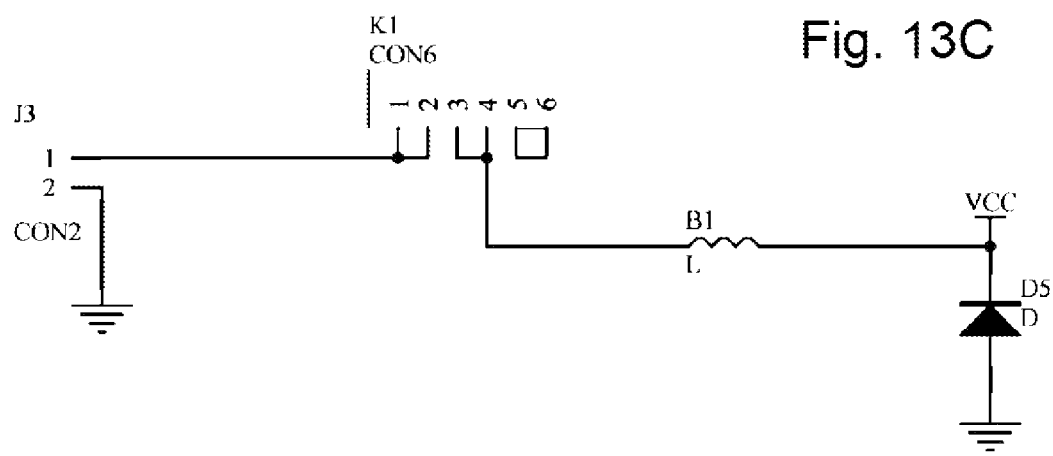
Figure 14A:
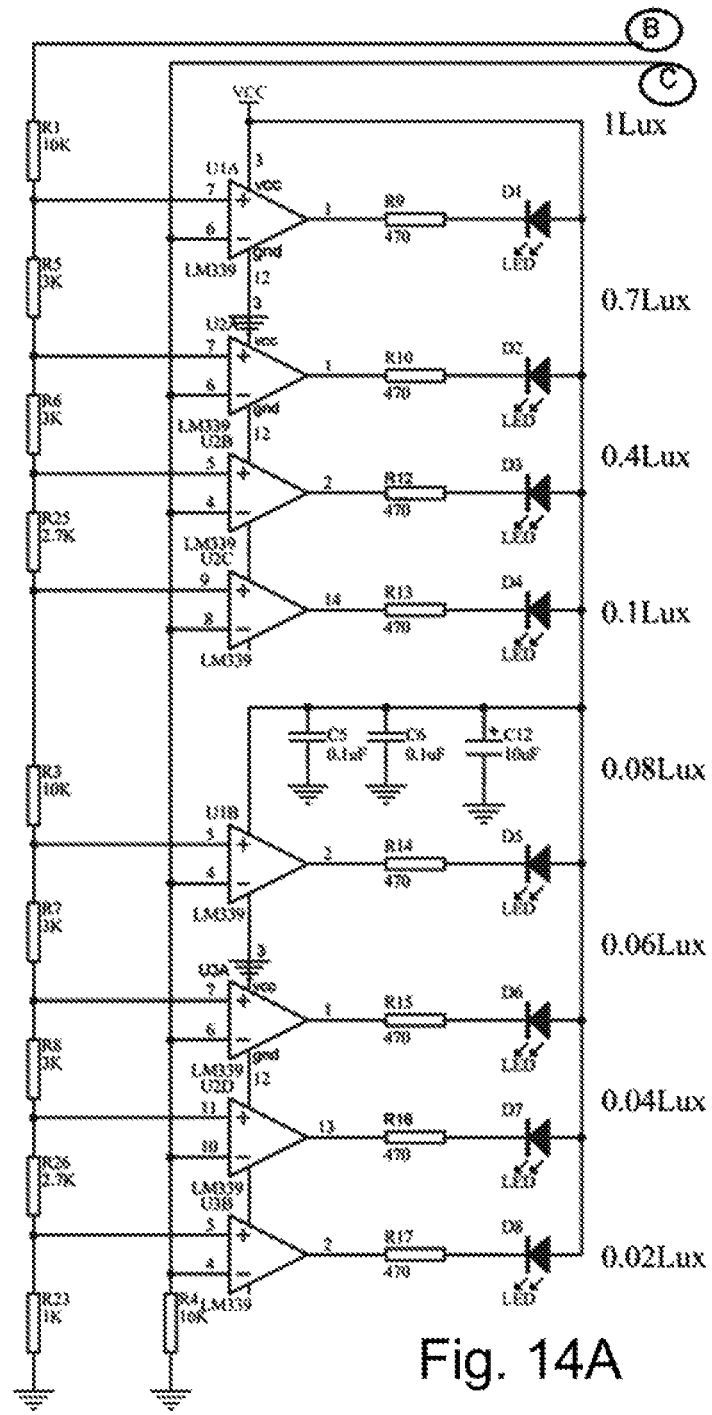
Figure 14B:
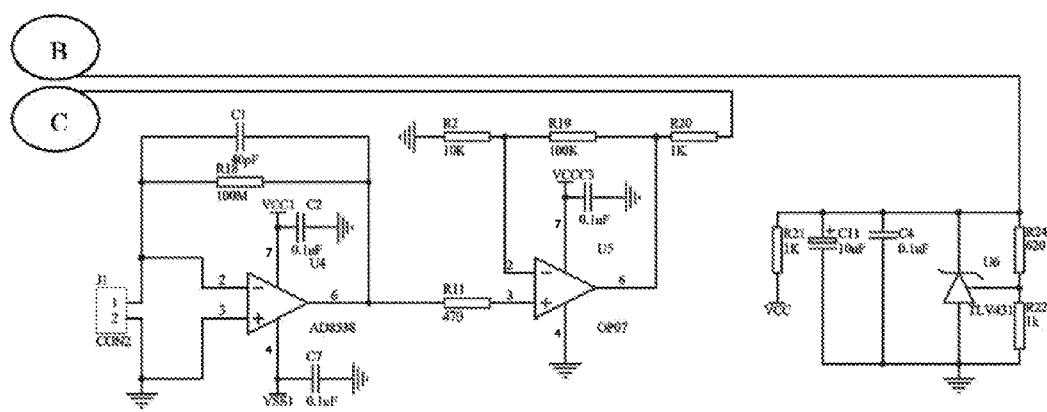
Figure 14C:
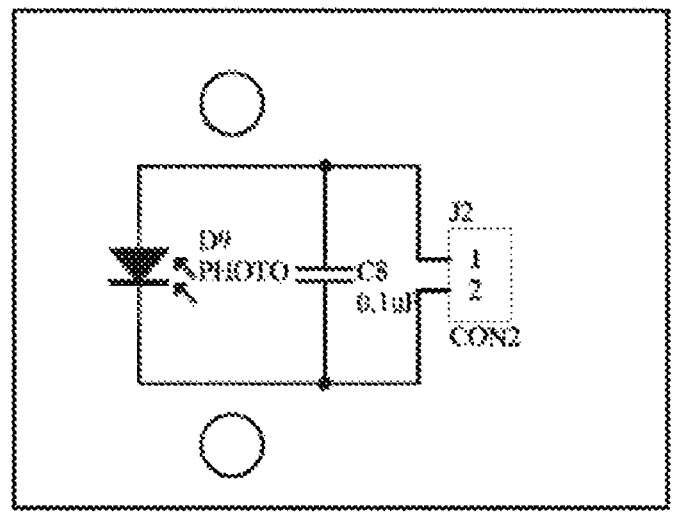
Figure 14D:
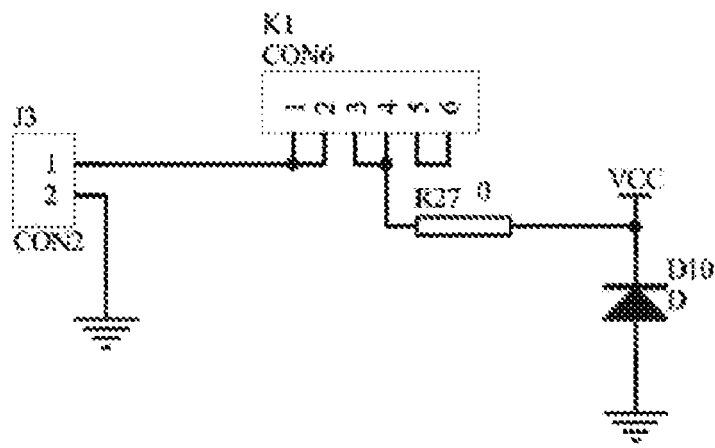
Figure 14E:
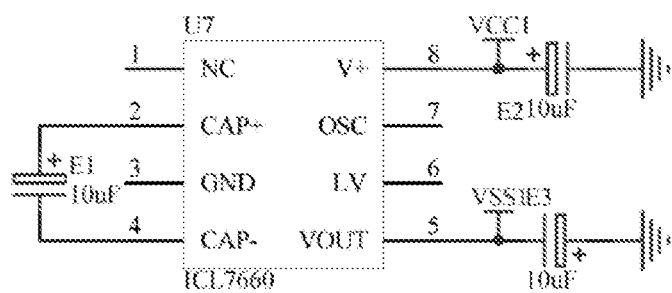
Figure 14F:
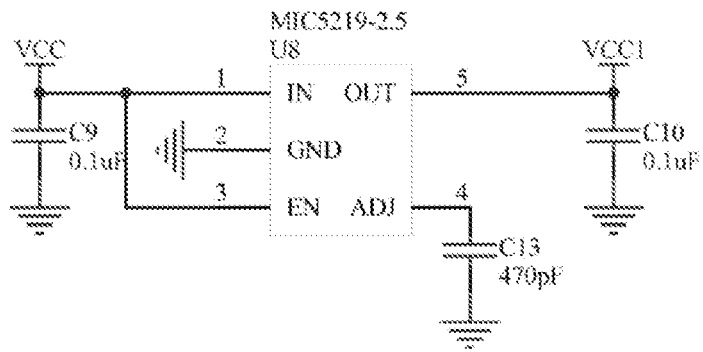
Figure 15:
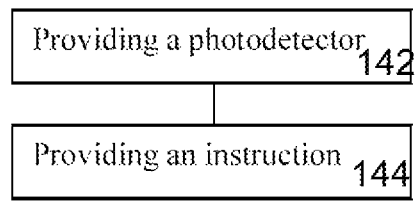

FIGS. 13A through 13D and 14A through 14 F are alternative circuit diagrams for the photodetector 38, amplifier 66 and display 68 of FIG. 3. The circuits of FIGS. 13A-D and 14A-F provide examples of photodetector 36 circuits that detect graduated differences in brightness due to the luminol-oxidizer reaction 2. The differences in brightness corresponds to different amounts of blood present in the urine or feces. The photodetectors 36 of FIGS. 13A-D and 14A-F are battery powered (CON1) devices (photometers) in which the photodiode (D9) converts incident light to current. The amount the light (current) from 0.1 to 1 Lux on FIG. 13A through D and 0.02 Lux to 1 Lux on FIG. 14A through F is displayed via a series of diodes (D1 to D4) and (D1 to D8) on FIG. 13A-D and FIG. 14A-F respectively. FIGS. 13A and 13B present a single circuit joined at element 'A.' FIGS. 14A and 14B are a single circuit joined at elements 'B' and 'C.'

FIG. 15 is a flow chart of a method of the Invention from the perspective of an equipment supplier or manufacturer. In step 142, the supplier or manufacturer provides a photodetector apparatus 36. The apparatus is configured as described above. The supplier or manufacturer also provides an instruction as to the how a user should use the apparatus for the detection of blood in urine or feces. The other aspects of the Invention are as described above.

LIST OF NUMBERED ELEMENTS a reaction 2
a luminol 4
an oxidizer 6
a water 8
a toilet bowl 10
a base 12
an iron 14
a light 16
a dispenser 30
tablets, powders, solutions and suspensions 32
a plurality of reservoirs 34
toilet tank 35
an actuator 36
a photodetector 38
toilet seat 40
a manually-operated control 42
a control configured to detect a weight on a toilet seat 44
a control configured to detect a change of position of said toilet seat 46
a control configured to detect a presence of a user 48
an effector 50
a solenoid valve 52
a photodiode 54
a charge-coupled device 56
an active pixel sensor 58
bandpass optical filter 60
a range of wavelengths of light from 410 nm to 490 nm 62
signal processing module 64
amplifier 66
display or alarm 68
amplifier circuit 70
potentiometer 72
a microprocessor 74
a photodetector signal 76
a computer memory 78
port 80
network connection 82
an instruction
enclosure 106
power supply 108
wires 110
dispenser 30
reservoir 34
valve 112
toilet 114
lid 118
hinge 120
underside 122
instruction 144

We claim:

1. An apparatus for detecting blood in urine or on feces, the apparatus comprising: a photodetector, said photodetector being configured to detect a light emitted by a reaction of a luminol and an oxidizer catalyzed by an iron in a water in a toilet bowl, said photodetector being located proximate to said water in said toilet bowl but not submerged within said water in said toilet bowl, whereby said photodetector is configured to detect said iron from a heme in the blood when the blood is present in the water in the toilet bowl along with said luminol and said oxidizer under alkaline conditions.

2. The apparatus of claim 1 wherein said photodetector is configured to detect a range of wavelengths of said light, said range of wavelengths of said light corresponding to said range of wavelengths of said light emitted by said reaction of said luminol and said oxidizer catalyzed by said iron or wherein said range of wavelengths of said light corresponding to a range of wavelengths of said light emitted by a fluorophore in said water in said toilet bowl when said fluorophore is excited by said light emitted by said reaction of said luminol and said oxidizer catalyzed by said iron.

3. The apparatus of claim 2 wherein said photodetector is select from a list consisting of a photodiode, a charge-coupled device and an active pixel sensor.

4. The apparatus of claim 2, the apparatus further comprising:
 a. a microprocessor, said microprocessor being operably connected to said photodetector, said photodetector being configured to generate a photodetector signal in response to said detected light, said photodetector signal having a value, said value corresponding to a brightness of said light, said microprocessor being configured to receive said photodetector signal;
 b. a computer memory, said computer memory being operably connected to said microprocessor, said microprocessor being configured to store said photodetector signal in said computer memory.

5. The apparatus of claim 4 wherein said microprocessor being configured to receive said photodetector signal at a first time, said photodetector signal at said first time defining a background signal, said background signal corresponding to said brightness of said light at said first time, said microprocessor being configured to receive said photodetector signal at a second time, said photodetector signal at said second time defining a sample signal, said photodetector signal at said second time corresponding to said brightness of said light at said second time, said second time being after said first time, said first time is selected to be a time when said luminol, said oxidizer and a base are present in said water in said toilet bowl but the feces or the urine is not present in said water in said toilet bowl and wherein said second time is selected to be said time after said first time when said luminol, said oxidizer and said base are present in said water in said toilet bowl and in addition the feces or the urine is present in the water in the toilet bowl, said microprocessor being configured to store said sample signal and said background signal in said computer memory.

6. The apparatus of claim 5 wherein said microprocessor is configured to compare said sample signal to said background signal, said microprocessor being configured to determine whether said sample signal exceeds said background signal to define a result, said result being that blood is detected in the urine or feces if said sample signal exceeds said background signal by more than a predetermined amount, said result being that blood is not detected in the urine or feces if said sample signal does not exceed said background signal by more than said predetermined amount.

7. The apparatus of claim 6 wherein said microprocessor is configured to determine whether said sample signal exceeds said background signal by any of a plurality of graduated increments to further define said result, said plurality of graduated increments corresponding to graduated amounts of blood present in the urine or feces, said microprocessor is configured to report said result to a user.

8. The apparatus of claim 6 wherein said microprocessor is configured for connection to a network, said network being a one of a local area network, a wide area network, an Internet and a wireless communications network, said microprocessor being configured to communicate said result over said communications network.

9. The apparatus of claim 5 wherein said microprocessor is configured to compare said sample signal to said background signal, said background signal and said sample signal corresponding to a one of a plurality of instances of urination or defecation by a user, each of said background signal and said sample signal being a one of a plurality of background signals and sample signals, each other of said background signals and sample signals corresponding to another of said plurality of instances of urination or defecation by said user, said microprocessor being configured to statistically evaluate said plurality of background signals and said plurality of sample signals to determine whether said sample signals exceed said background signals by a statistically significant amount, said microprocessor being configured to determine a positive result for said blood in said urine or said feces if said microprocessor determines that said sample signal exceeds said background signal by said statistically significant amount.

10. The apparatus of claim 5, the apparatus further comprising: an actuator, wherein said actuator is configured to activate said photodetector, said actuator is configured to be actuated by a motion or position of a toilet seat or a toilet lid, by a pressure on said toilet seat, or by a detected presence of a user.

11. The apparatus of claim 10 wherein said photodetector signal has a value, said photodetector is configured to detect said light continuously upon activation by said actuator and to generate said photodetector signal, said microprocessor is configured to record said photodetector signal continuously to computer memory, said microprocessor is configured to select said second time based upon a one of a passage of time, an activation of said actuator by said user, or by said value of said photodetector signal.

12. The apparatus of claim 1 wherein said photodetector is configured to detect a range of wavelengths of said light, said range of wavelengths of said light corresponding to said range of wavelengths of said light emitted by said reaction of said luminol and said oxidizer catalyzed by said iron in said water of said toilet bowl, said photodetector being configured not to detect said light substantially outside of said range of wavelengths of said light emitted by said reaction of said luminol and said oxidizer catalyzed by said iron in said water of said toilet bowl.

13. The apparatus of claim 12 wherein said range of wavelengths of said light is substantially from 410 nm to 490 nm.

14. The apparatus of claim 1, the apparatus further comprising: a dispenser, said dispenser configured to dispense an amount of said luminol, said oxidizer and a base into the water in the toilet bowl sufficient to cause said luminol to luminesce in the presence of the blood in the toilet bowl water in greater than a predetermined concentration.

15. The apparatus of claim 14 wherein said luminol, said oxidizer and said base are in a form selected from a list consisting of tablets, powders, sachets, solutions and suspensions.

16. The apparatus of claim 14 wherein said dispenser having a plurality of reservoirs, said plurality of reservoirs being configured to contain said luminol, said oxidizer and said base, said dispenser having a configuration to charge said water in said toilet bowl with said luminol, said oxidizer and said base.

17. The apparatus of claim 16 wherein said configuration of said dispenser to charge said water comprising:
   a. an actuator, said actuator being operable by a user, said actuator is selected from a list consisting of a manually-operated control, a control configured to detect a weight on a toilet seat, a control configured to detect a change of position of said toilet seat, and a control configured to detect a presence of a user;
   b. an effector, said effector being operably connected to said actuator, said effector being configured to dispense said luminol, said oxidizer and said base into said water upon activation of said actuator by said user.

18. The apparatus of claim 17, the apparatus further comprising: a flush toilet, said flush toilet include the toilet bowl, said actuator being a flushing actuator, said flushing actuator being configured to flush said flush toilet upon activation of said flushing actuator by said user, said effector dispensing said luminol, said oxidizer and said base into said water in said toilet bowl upon a re-filling of said toilet bowl with said water after actuation of said flushing actuator.

19. The apparatus of claim 1 wherein the toilet bowl having a toilet seat, said photodetector being operably mounted to said toilet seat, said photodetector being configured to detect said light when a user is sitting on said toilet seat, whereby said user sufficiently blocks entry into the toilet bowl of an ambient light to allow said photodetector to detect said light emitted by said reaction of said luminol in said water of the toilet bowl.

20. The apparatus of claim 1 wherein the toilet bowl having a toilet seat and a toilet lid, said toilet lid selectably covering said toilet bowl and having an open and a closed position, said photodetector being operably mounted to said toilet lid or said toilet seat to detect said light when said lid is in said closed position, whereby said toilet seat and said toilet lid sufficiently block entry into the toilet bowl of an ambient light to allow said photodetector to detect said light emitted by said reaction of said luminol in said water of the toilet bowl.

21. An apparatus for detecting blood in urine or feces, the apparatus comprising:

a. a toilet having a toilet bowl containing a water,
b. a photodetector, said photodetector being configured to detect a light emitted by a reaction of a luminol and an oxidizer catalyzed by an iron in said water in said toilet bowl, said photodetector being located proximate to said water in said toilet bowl but not submerged within said water in said toilet bowl, whereby said photodetector is configured to detect an iron from a heme in the blood when the blood is present in the water in the toilet bowl along with said luminol and said oxidizer under alkaline conditions.

22. The apparatus of claim 21 wherein said photodetector is configured to detect a range of wavelengths of said light, said range of wavelengths of said light corresponding to said range of wavelengths of said light emitted by said reaction of said luminol and said oxidizer catalyzed by said iron.

23. The apparatus of claim 22 wherein said photodetector is configured not to detect said light substantially outside of said range of wavelengths of said light emitted by said reaction of said luminol and said oxidizer catalyzed by said iron in said water of said toilet bowl.

24. The apparatus of claim 22, the apparatus further comprising:
a. a microprocessor, said microprocessor being operably connected to said photodetector, said photodetector being configured to generate a photodetector signal in response to said detected light, said photodetector signal having a value, said value corresponding to a brightness of said light, said microprocessor being configured to receive said photodetector signal at a first time, said photodetector signal at said first time defining a background signal, said background signal corresponding to said brightness of said light at said first time, said microprocessor being configured to receive said photodetector signal at a second time, said photodetector signal at said second time defining a sample signal, said sample signal corresponding to said brightness of said light at said second time, said second time being after said first time;
b. a computer memory, said computer memory being operably connected to said microprocessor, said microprocessor being configured to store said sample signal and said background signal in said computer memory.

25. The apparatus of claim 24 wherein said first time is selected to be a time when said luminol, said oxidizer and a base are present in said water in said toilet bowl but the feces or the urine is not present in said water in said toilet bowl and wherein said second time is selected to be said time after said first time when said luminol, said oxidizer and said base are present in said water in said toilet bowl and in addition the feces or the urine is present in the water in the toilet bowl.

26. The apparatus of claim 24 wherein said microprocessor is configured to compare said sample signal to said background signal, said microprocessor being configured to determine whether said sample signal exceeds said background signal to define a result, said result being that blood is detected in the urine or feces if said sample signal exceeds said background signal by more than a predetermined amount, said result being that blood is not detected in the urine or feces if said sample signal does not exceed said background signal by more than said predetermined amount.

27. The apparatus of claim 26, the apparatus further comprising: a display operably connected to said microprocessor, said display being configured to display said result to a user.

28. The apparatus of claim 26 wherein said microprocessor is configured to determine whether said sample signal exceeds said background signal by any of a plurality of graduated increments to further define said result, each of said plurality of graduated increments corresponding to a one of a plurality of graduated amounts of blood present in the urine or feces, the apparatus further comprising: a display operably connected to said microprocessor, wherein said microprocessor is configured to display said result.

29. The apparatus of claim 26 wherein said microprocessor is configured for connection to a network, said network being a one of a local area network, a wide area network, an Internet and a wireless communications network, said microprocessor being configured to communicate said result over said network.

30. The apparatus of claim 21, the apparatus further comprising: a dispenser, said dispenser having a configuration to charge said luminol, said oxidizer and a base into said water in said toilet bowl in amounts sufficient to cause said luminol to fluoresce in a presence of the blood in said water in greater than a predetermined concentration, when the blood is present in said water.

31. The apparatus of claim 30 wherein said configuration of said dispenser to charge said water comprising:
a. an actuator, said actuator being operable by a user;
b. an effector, said effector being operably connected to said actuator, said effector being configured to dispense said luminol, said oxidizer and said base into said water upon activation of said actuator by said user.

32. A method of providing an apparatus for detecting blood in urine or feces in a water in a toilet bowl, the method comprising:
a. providing a photodetector, said photodetector being configured to detect a light emitted in the water in the toilet bowl by a reaction of a luminol and an oxidizer and catalyzed by an iron present in the blood in the water in the toilet bowl when said photodetector is located proximate to said water in said toilet bowl but not submerged within the water in the toilet bowl and blood is present in the water in the toilet bowl under adequately alkaline conditions;
b. providing an instruction, said instruction instructing a user to:
   i. add said luminol and said oxidizer to said water;
   ii. add the urine or feces to the water after adding said luminol and said oxidizer to said water.

33. The method of claim 32 wherein said photodetector generates a photodetector signal in response to said detected light at a first time and at a second time, said photodetector signal having a value, said value corresponding to a brightness of said light, said photodetector signal at said first time defining a background signal, said background signal corresponding to said brightness of said light at said first time, said photodetector signal at said second time defining a sample signal, said sample signal corresponding to said brightness of said light at said second time, said second time being after said first time, said first time being selected to be after said luminol and said oxidizer are added to said water and before the feces or the urine is added to the water, said second time being after said first time and being after the feces or the urine is added to the water.

34. The method of claim 33 wherein said photodetector compares said sample signal to said background signal to define a result, said result being positive for the blood in the urine or feces when said value of said sample signal exceeds said value of said background signal by more than a predetermined amount, said result being negative for the blood in the urine or feces when said sample signal does not exceed said background signal by more than said predetermined amount.

35. The method of claim 34 wherein said photodetector further comprising a microprocessor operably attached to said photodetector and a computer memory operably connected to said microprocessor, said microprocessor compares said sample signal and said background signal to define said result.

36. The method of claim 35 wherein said microprocessor determines whether said value of said sample signal exceeds said value of said background signal by any of a plurality of increments to define said result.

37. The method of claim 36 wherein said microprocessor displays said result to said user.

38. The method of claim 35 wherein said microprocessor is operably connected to a network, said network being selected from the list consisting of a local area network, a wide area network, an Internet, and a wireless communications network, said microprocessor communicating said result over said network.

39. The method of claim 32 wherein said step of providing said instruction to said user, said instruction instructing said user to add said luminol and said oxidizer to the water, comprising: instructing said user to activate a dispenser, said dispenser dispensing an effective amount of said luminol, an effective amount of said oxidizer and an effective amount of a base to the water in the toilet bowl.

40. A method of testing urine or feces in a water in a toilet bowl for a presence of blood, the method comprising:
 a. receiving by a user of a photodetector, said photodetector being configured to detect a light emitted in the water in the toilet bowl by a reaction of a luminol and an oxidizer and catalyzed by an iron present in the blood in the water in the toilet bowl when blood is present in the water in the toilet bowl;
 b. locating said photodetector proximate to the water in the toilet bowl but not submerged within the water in the toilet bowl;
 c. adding said luminol and said oxidizer to the water;
 d. adding the urine or feces to the water after adding said luminol and said oxidizer to the water;
 e. detecting by said photodetector of whether said light is emitted in the water of the toilet bowl.

41. The method of claim 40 wherein said photodetector generates a photodetector signal in response to said detected light at a first time and at a second time, said photodetector signal having a value, said value corresponding to a brightness of said light, said photodetector signal at said first time defining a background signal, said background signal corresponding to said brightness of said light at said first time, said photodetector signal at said second time defining a sample signal, said sample signal corresponding to said brightness of said light at said second time, said second time being after said first time, said first time being selected to be after said luminol and said oxidizer are added to the water and before the feces or the urine is added to the water, said second time being after said first time and being after the feces or the urine is added to the water, the method further comprising:
 a. detecting said light at said first time; and
 b. detecting said light at said second time.

42. The method of claim 41 wherein said photodetector compares said sample signal to said background signal to define a result, said result being positive for the blood in the urine or feces when said value of said sample signal exceeds said value of said background signal by more than a predetermined amount, said result being negative for the blood in the urine or feces when said sample signal does not exceed said background signal by more than said predetermined amount.

43. The method of claim 42 wherein said photodetector further comprising a microprocessor operably attached to said photodetector and a computer memory operably connected to said microprocessor, said microprocessor compares said sample signal and said background signal to define said result.

44. The method of claim 43 wherein said microprocessor determines whether said value of said sample signal exceeds said value of said background signal by any of a plurality of graduated increments to define said result, each of said plurality of graduated increments corresponding to a one of a plurality of amounts of the blood in the water.

45. The method of claim 44 wherein said microprocessor displays said result to said user, the method further comprising: observing said result by said user.

46. The method of claim 43 wherein said microprocessor is operably connected to a network, said network being selected from the list consisting of a local area network, a wide area network, an Internet, and a wireless communications network, said microprocessor communicating said result over said network.

47. The method of claim 40 wherein said step of adding said luminol and said oxidizer to the water comprising: activating a dispenser, said dispenser dispensing an effective amount of said luminol, an effective amount of said oxidizer and an effective amount of a base to the water in the toilet bowl.

\* \* \* \* \*